US010898596B2

(12) United States Patent
Vlahov et al.

(10) Patent No.: US 10,898,596 B2
(45) Date of Patent: *Jan. 26, 2021

(54) CONJUGATES FOR IMAGING

(71) Applicant: Endocyte, Inc., West Lafayette, IN (US)

(72) Inventors: Iontcho R. Vlahov, West Lafayette, IN (US); Christopher P. Leamon, West Lafayette, IN (US); Hari Krishna R. Santhapuram, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 44 days.

This patent is subject to a terminal disclaimer.

(21) Appl. No.: 16/229,785

(22) Filed: Dec. 21, 2018

(65) Prior Publication Data
US 2019/0134236 A1 May 9, 2019

Related U.S. Application Data

(63) Continuation of application No. 14/989,498, filed on Jan. 6, 2016, now Pat. No. 10,188,759.

(60) Provisional application No. 62/100,677, filed on Jan. 7, 2015.

(51) Int. Cl.
*A61K 51/02* (2006.01)
*A61K 51/04* (2006.01)

(52) U.S. Cl.
CPC .......... *A61K 51/0459* (2013.01); *A61K 51/02* (2013.01)

(58) Field of Classification Search
CPC ............ A61K 51/0459; A61K 49/0043; A61K 51/0497; A61K 47/542; A61K 47/45
See application file for complete search history.

(56) References Cited

U.S. PATENT DOCUMENTS

| 4,691,024 A | 9/1987 | Shirahata et al. |
|---|---|---|
| 4,713,249 A | 12/1987 | Schroder |
| 5,103,018 A | 4/1992 | Motomichi et al. |
| 5,266,333 A | 11/1993 | Cady et al. |
| 5,418,982 A | 5/1995 | Kishi et al. |
| 5,627,165 A | 5/1997 | Glazier et al. |
| 5,795,877 A | 8/1998 | Jackson et al. |
| 5,863,536 A | 1/1999 | Jackson et al. |
| 5,866,679 A | 2/1999 | DeFeo-Jones et al. |
| 5,902,817 A | 5/1999 | Jackson et al. |
| 5,948,750 A | 9/1999 | Garsky et al. |
| 5,962,237 A | 10/1999 | Ts'o et al. |
| 5,962,521 A | 10/1999 | Jackson et al. |
| 5,968,915 A | 10/1999 | Jackson et al. |
| 5,998,362 A | 12/1999 | Feng et al. |
| 6,054,444 A | 4/2000 | Jackson et al. |
| 6,127,333 A | 10/2000 | Brady et al. |
| 6,174,858 B1 | 1/2001 | Brady et al. |
| 6,177,404 B1 | 1/2001 | DeFeo-Jones et al. |
| 6,232,287 B1 | 5/2001 | Ruoslahti et al. |
| 6,368,598 B1 | 4/2002 | D'Amico et al. |
| 6,391,305 B1 | 5/2002 | Feng et al. |
| 6,428,785 B1 | 8/2002 | Gokcen et al. |
| 6,479,470 B1 | 11/2002 | Kozikowski et al. |
| 6,528,499 B1 | 3/2003 | Kozikowski et al. |
| 6,692,724 B1 | 2/2004 | Yang et al. |
| 6,875,886 B2 | 4/2005 | Frangioni et al. |
| 6,946,133 B1 | 9/2005 | Schlom et al. |
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |
| 7,192,586 B2 | 3/2007 | Bander et al. |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,399,460 B2 | 7/2008 | Wedeking et al. |
| 7,408,079 B2 | 8/2008 | Pomper et al. |
| 7,485,299 B2 | 2/2009 | Afar et al. |
| 7,514,078 B2 | 4/2009 | Bander et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |

(Continued)

FOREIGN PATENT DOCUMENTS

| CA | 2606138 | 10/2005 |
|---|---|---|
| CN | 101863924 | 10/2010 |

(Continued)

OTHER PUBLICATIONS

PCT International Search Report/Written Opinion for PCT/US2009/061067, completed May 28, 2010.
PCT International Search Report for PCT/US2008/073375 dated Oct. 26, 2008.
PCT International Search Report for PCT/US2016/012653 dated Mar. 11, 2016.

(Continued)

*Primary Examiner* — Sudhakar Katakam

(74) *Attorney, Agent, or Firm* — Barnes & Thornburg LLP

(57) ABSTRACT

The invention described herein relates to conjugates and compositions for imaging, diagnosing, and/or monitoring diseases using radionuclide-based imaging. In particular, the invention described herein relates to conjugates and compositions for imaging, diagnosing, and/or monitoring diseases using positron emission tomography.

21 Claims, No Drawings

(56) References Cited

U.S. PATENT DOCUMENTS

| | | |
|---|---|---|
| 7,767,803 B2 | 8/2010 | Diener et al. |
| 7,794,929 B2 | 9/2010 | Baylin et al. |
| 7,862,798 B2 | 1/2011 | Leamon et al. |
| 7,872,235 B2 | 1/2011 | Rousso et al. |
| 7,875,586 B2 | 1/2011 | Kovbasnjuk et al. |
| 7,879,981 B2 | 2/2011 | Obata et al. |
| 7,910,594 B2 | 3/2011 | Vlahov et al. |
| RE42,275 E | 4/2011 | Berkman |
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen et al. |
| 8,211,401 B2 | 7/2012 | Babich et al. |
| 8,211,402 B2 | 7/2012 | Babich et al. |
| 8,211,473 B2 | 7/2012 | Troiano et al. |
| 8,211,635 B2 | 7/2012 | Barton |
| 8,227,634 B2 | 7/2012 | Pomper et al. |
| 8,236,330 B2 | 8/2012 | Zale et al. |
| 8,246,968 B2 | 8/2012 | Zale et al. |
| 8,258,111 B2 | 9/2012 | Shen et al. |
| 8,273,363 B2 | 9/2012 | Zale et al. |
| 8,313,728 B2 | 11/2012 | Leamon et al. |
| 8,388,977 B2 | 3/2013 | Low et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,487,128 B2 | 7/2013 | Weissbach et al. |
| 8,487,129 B2 | 7/2013 | Babich et al. |
| 8,507,434 B2 | 8/2013 | Popel et al. |
| 8,557,772 B2 | 10/2013 | Popel et al. |
| 8,562,945 B2 | 10/2013 | Babich et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,709,483 B2 | 4/2014 | Farokhzad et al. |
| 8,772,226 B2 | 7/2014 | Denmeade et al. |
| 8,772,459 B2 | 7/2014 | Ho et al. |
| 8,778,305 B2 | 7/2014 | Pomper et al. |
| 8,802,153 B2 | 8/2014 | Cheng et al. |
| 8,816,095 B2 | 8/2014 | Brown et al. |
| 8,834,842 B2 | 9/2014 | Leamon et al. |
| 8,840,865 B2 | 9/2014 | Babich et al. |
| 8,852,630 B2 | 10/2014 | Spiegel et al. |
| 8,859,509 B2 | 10/2014 | Spiegel et al. |
| 8,865,126 B2 | 10/2014 | Leamon et al. |
| 8,877,970 B2 | 11/2014 | Zimmerman et al. |
| 8,901,294 B2 | 12/2014 | Kim et al. |
| 8,907,058 B2 | 12/2014 | Low et al. |
| 8,916,167 B2 | 12/2014 | Low et al. |
| 8,926,944 B2 | 1/2015 | Babich et al. |
| 8,926,945 B2 | 1/2015 | Port et al. |
| 8,940,871 B2 | 1/2015 | Wu et al. |
| 8,946,388 B2 | 2/2015 | Sahin et al. |
| 8,962,799 B2 | 2/2015 | Babich et al. |
| 8,987,319 B2 | 3/2015 | Miller et al. |
| 9,044,468 B2 | 6/2015 | Pomper et al. |
| 9,056,841 B2 | 6/2015 | Pomper et al. |
| 9,193,763 B2 | 11/2015 | Low et al. |
| 9,226,981 B2 | 1/2016 | Pomper et al. |
| 9,242,012 B2 | 1/2016 | Ma et al. |
| 9,278,067 B2 | 3/2016 | Boulikas et al. |
| 9,295,727 B2 | 3/2016 | Zale et al. |
| 9,309,193 B2 | 4/2016 | Babich et al. |
| 9,636,413 B2 | 5/2017 | Vlahov et al. |
| 9,687,572 B2 | 6/2017 | Babich et al. |
| 9,951,324 B2 | 4/2018 | Low et al. |
| 10,188,759 B2 * | 1/2019 | Vlahov .............. A61K 51/0459 |
| 2001/0031252 A1 | 10/2001 | Low et al. |
| 2002/0001782 A1 | 1/2002 | Watanabe et al. |
| 2002/0055121 A1 | 5/2002 | Vielkind et al. |
| 2002/0103136 A1 | 8/2002 | Feng et al. |
| 2002/0115596 A1 | 8/2002 | Garsky et al. |
| 2002/0132983 A1 | 9/2002 | Junghans et al. |
| 2003/0035804 A1 | 2/2003 | D'Amico et al. |
| 2003/0086900 A1 | 5/2003 | Low et al. |
| 2003/0133927 A1 | 7/2003 | DeFeo-Jones et al. |
| 2003/0138432 A1 | 7/2003 | Glazier et al. |
| 2003/0207808 A1 | 11/2003 | Savitzky et al. |
| 2003/0215456 A1 | 11/2003 | Yao et al. |
| 2003/0220241 A1 | 11/2003 | DeFeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs et al. |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0110723 A1 | 6/2004 | Frangioni et al. |
| 2004/0146516 A1 | 7/2004 | Roben et al. |
| 2004/0213791 A1 | 10/2004 | Bander et al. |
| 2004/0229845 A1 | 11/2004 | Frangioni et al. |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic |
| 2005/0245486 A1 | 11/2005 | Frangioni et al. |
| 2005/0255042 A1 | 11/2005 | Lam et al. |
| 2006/0024317 A1 | 2/2006 | Boyd et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud et al. |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020327 A1 | 1/2007 | Fikes et al. |
| 2007/0031326 A1 | 2/2007 | Shirvan et al. |
| 2007/0031438 A1 | 2/2007 | Junghans et al. |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier et al. |
| 2007/0179100 A1 | 8/2007 | Manoharan et al. |
| 2007/0219165 A1 | 9/2007 | Berkman et al. |
| 2007/0225213 A1 | 9/2007 | Kosak et al. |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008649 A1 | 1/2008 | Cappelletti |
| 2008/0008719 A1 | 1/2008 | Bowdish et al. |
| 2008/0089869 A1 | 4/2008 | Denmeade et al. |
| 2008/0114153 A1 | 5/2008 | Steeves et al. |
| 2008/0175789 A1 | 7/2008 | Frangioni et al. |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0214636 A1 | 8/2009 | Low et al. |
| 2009/0247614 A1 | 10/2009 | Manoharan et al. |

(56) References Cited

U.S. PATENT DOCUMENTS

| | | |
|---|---|---|
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman et al. |
| 2010/0209343 A1 | 8/2010 | Bander et al. |
| 2010/0240701 A1 | 9/2010 | Vlahov et al. |
| 2010/0324008 A1 | 12/2010 | Low et al. |
| 2011/0008253 A1 | 1/2011 | Babich et al. |
| 2011/0027180 A1 | 2/2011 | Magnani et al. |
| 2011/0027274 A1 | 2/2011 | Cheng et al. |
| 2011/0064657 A1 | 3/2011 | Pomper et al. |
| 2011/0142760 A1 | 6/2011 | Pomper et al. |
| 2011/0172254 A1 | 7/2011 | Leamon et al. |
| 2011/0176998 A1 | 7/2011 | Pomper et al. |
| 2011/0200677 A1 | 8/2011 | Chandran et al. |
| 2011/0288152 A1 | 11/2011 | Low et al. |
| 2012/0009121 A1 | 1/2012 | Pomper et al. |
| 2012/0276162 A1 | 11/2012 | Zale et al. |
| 2012/0322741 A1* | 12/2012 | Low .................. A61K 49/0043 514/19.5 |
| 2013/0034494 A1 | 2/2013 | Babich et al. |
| 2013/0172406 A1 | 7/2013 | Zale et al. |
| 2013/0336888 A1 | 12/2013 | Babich et al. |
| 2014/0107316 A1 | 4/2014 | Vlahov et al. |
| 2014/0140925 A1 | 5/2014 | Leamon et al. |
| 2014/0154702 A1 | 6/2014 | Parker et al. |
| 2014/0187501 A1 | 7/2014 | Bilodeau et al. |
| 2014/0314864 A1 | 10/2014 | Cheng et al. |
| 2015/0023875 A1 | 1/2015 | Farokhzad et al. |
| 2015/0079001 A1 | 3/2015 | Pomper et al. |
| 2015/0104387 A1 | 4/2015 | Pomper et al. |
| 2015/0110715 A1 | 4/2015 | Eder et al. |
| 2015/0246144 A1 | 9/2015 | Pomper et al. |
| 2015/0297735 A1 | 10/2015 | Vlahov et al. |
| 2015/0315196 A1 | 11/2015 | Howard et al. |
| 2015/0366968 A1 | 12/2015 | Basilion et al. |
| 2016/0067341 A1 | 3/2016 | Low et al. |
| 2016/0074526 A1 | 3/2016 | Bilodeau et al. |
| 2016/0114060 A1 | 4/2016 | Pomper et al. |
| 2016/0151508 A1 | 6/2016 | Low et al. |
| 2016/0220694 A1 | 8/2016 | Vlahov et al. |
| 2016/0287731 A1 | 10/2016 | Vlahov et al. |
| 2016/0361376 A1 | 12/2016 | Vlahov et al. |
| 2016/0361432 A1 | 12/2016 | Vlahov et al. |
| 2016/0361433 A1 | 12/2016 | Vlahov et al. |

FOREIGN PATENT DOCUMENTS

| | | |
|---|---|---|
| EP | 0116208 | 8/1984 |
| EP | 1177200 | 6/2005 |
| EP | 1472541 | 9/2009 |
| EP | 2170075 | 4/2010 |
| EP | 2318366 | 5/2011 |
| EP | 2136788 | 10/2011 |
| EP | 2373621 | 10/2011 |
| EP | 2389361 | 11/2011 |
| EP | 2644192 | 10/2013 |
| EP | 2644594 | 10/2013 |
| EP | 2648766 | 10/2013 |
| EP | 2436376 | 7/2014 |
| EP | 2759535 | 7/2014 |
| EP | 2240171 | 8/2014 |
| EP | 2823826 | 1/2015 |
| EP | 2097111 | 7/2015 |
| EP | 2921482 | 9/2015 |
| EP | 2938364 | 11/2015 |
| EP | 2942065 | 11/2015 |
| EP | 2958596 | 12/2015 |
| EP | 2993171 | 3/2016 |
| EP | 2706057 | 4/2016 |
| EP | 3038996 | 7/2016 |
| EP | 2408755 | 5/2017 |
| JP | 2002-506204 | 2/2002 |
| JP | 2004-536034 | 12/2004 |
| JP | 2005-274569 | 10/2005 |
| JP | 2006-501149 | 1/2006 |
| JP | 2006514961 | 5/2006 |
| JP | 2006-518712 | 8/2006 |
| JP | 2007-521803 | 8/2007 |
| JP | 2009-519209 A | 5/2009 |
| JP | 2010-515732 A | 5/2010 |
| JP | 2010-518112 A | 5/2010 |
| JP | 2011-132258 | 7/2011 |
| WO | WO 1988/001622 | 3/1988 |
| WO | WO 1991007418 | 5/1991 |
| WO | 1995033766 | 12/1995 |
| WO | WO 99/45374 | 9/1999 |
| WO | WO 2000/064911 | 11/2000 |
| WO | WO2000/066091 | 11/2000 |
| WO | WO 2002/043773 | 6/2002 |
| WO | WO 2002/062398 | 8/2002 |
| WO | WO 2002098885 | 12/2002 |
| WO | 2003/000201 | 1/2003 |
| WO | WO 2003060523 | 7/2003 |
| WO | WO 2003/092742 | 11/2003 |
| WO | WO 2003097647 | 11/2003 |
| WO | WO 2004/010957 | 2/2004 |
| WO | 2004069285 | 8/2004 |
| WO | WO 2004/069159 | 8/2004 |
| WO | WO 2005/082023 | 9/2005 |
| WO | WO 2006012527 | 2/2006 |
| WO | WO 2006/096754 | 9/2006 |
| WO | WO 2006093991 | 9/2006 |
| WO | WO 2006/136564 | 12/2006 |
| WO | 2007/006041 | 1/2007 |
| WO | WO 2007/022494 | 2/2007 |
| WO | WO 2007/042504 | 4/2007 |
| WO | WO 2007/106869. | 9/2007 |
| WO | WO 2008/058192 | 5/2008 |
| WO | WO 2008057437 | 5/2008 |
| WO | 2008/088648 | 7/2008 |
| WO | 2008/098112 | 8/2008 |
| WO | 2008/101231 | 8/2008 |
| WO | WO 2008/121949 | 10/2008 |
| WO | WO 2009/002529 | 12/2008 |
| WO | WO 2009/026177 | 2/2009 |
| WO | WO 2009/070302 | 6/2009 |
| WO | 2009089383 | 7/2009 |
| WO | WO 2009082606 | 7/2009 |
| WO | WO 2009002993 | 12/2009 |
| WO | WO 2010/014933 | 2/2010 |
| WO | WO 2010/065899 | 6/2010 |
| WO | WO 2010/065902 | 6/2010 |
| WO | WO 2010/065906 | 6/2010 |
| WO | WO 2010/108125 | 9/2010 |
| WO | WO 2011/014821 | 2/2011 |
| WO | WO 2011/106639 | 9/2011 |
| WO | WO 2012/078534 | 6/2012 |
| WO | WO 2012/166923 | 12/2012 |
| WO | WO 2013/028664 | 2/2013 |
| WO | WO 2013022797 | 2/2013 |
| WO | WO2013/130776 | 9/2013 |
| WO | 2014/062697 | 4/2014 |
| WO | WO 2014078484 | 5/2014 |
| WO | WO 2014/106208 | 7/2014 |
| WO | WO 2014/127365 | 8/2014 |
| WO | WO 2014/134543 | 9/2014 |
| WO | WO 2015/055318 | 4/2015 |
| WO | WO 2015/057250 | 4/2015 |
| WO | WO 2015/171792 | 11/2015 |
| WO | WO 2016/030329 | 3/2016 |
| WO | WO 2016/040179 | 3/2016 |

OTHER PUBLICATIONS

Davis, Mindy I., et al., "Crystal Structure of Prostate-Specific Membrane Antigen, A Tumor Marker and Peptidase", Apr. 26, 2005, PNAS, vol. 102, No. 17, pp. 5981-5986.

(56) References Cited

OTHER PUBLICATIONS

Jackson, Paul F., et al., "Design of NAALADase Inhibitors: A Novel Neuroprotective Strategy", 2001, Current Medicinal Chemistry, vol. 8, No. 8, pp. 949-957.
Kozikowski, Alan P., et al., "Design of Remarkably Simple, Yet Potent Urea-Based Inhibitors of Glutamate Carbozypeptidase II (NAALADase)"2, 2001, Journal of Medicinal Chemistry, vol. 44, No. 3, pp. 298-301.
Kozikowski, Alan P., et al., "Synthesis of Urea-Based Inhibitors as Active Site Probes of Glutamate Carboxypeptidase II: Efficacy as Analgesic Agents", 2004, Journal of Medicinal Chemistry, vol. 47, No. 7, pp. 1729-1738.
Majer, Pavel., et al., "Synthesis and Biological Evaluation of Thiol-Based Inhibitors og Glutamate Carboxypeptidase II: Discovery of an Orally Active GCP II Inhibitor", 2003, Journal of Medicinal Chemistry, vol. 46, No. 10, pp. 1989-1996.
Mesters, et al., et al., "Structure of Glutamate Carboxypeptidase II, a Drug Target in Neuronal Damage and Prostate Cancer"2, 2006, The EMBO Journal, vol. 25, No. 6, pp. 1375-1384.
Ranasinghe, M. G., et al., "Facile Synthesis of Unsymmetrical Thiolsulfonates via Sulfonylation of Mercaptans", 1988, Synthetic Communications, vol. 18, No. 3, pp. 227-232.
Olsnes, S., et al., Immunology Today, 10, pp. 291-295 (1989).
Melby, et at., Cancer Research 53(8), pp. 1755-1760 (1993).
Truffert, et al., Tetrahedron, 52:3005 (1996).
Martin, et al., Helv. Chim. Acta, 78, 486-504 (1995) and Abstract.
Lupold, et al., "Identification and characterization of nuclease-stabilized RNA molecules that bind human prostate cancer cells via the prostate-specific membrane antigen." Cancer Res. 2002; 62:4029-4033.
Farokhzad, et al., "Nanoparticle-Aptamer Bioconjugates: A New Approach for Targeting Prostate Cancer Cells," Cancer Research 64, pp. 7668-7672 (2004).
PCT International Search Report/Written Opinion for PCT/US2009/061049, completed Mar. 15, 2010.
Jayaprakash, Sarva, et al. "Design and synthesis of a PSMA inhibitor—doxorubicin conjugate for targeted prostate cancer therapy." ChemMedChem 1.3 (2006): 299-302.
PCT International Search Report and Written Opinion for PCT/US2011/026238, dated Apr. 27, 2011.
Foss, Catherine A., et al. "Radiolabeled small-molecule ligands for prostate-specific membrane antigen: in vivo imaging in experimental models of prostate cancer." *Clinical cancer research* 11.11 (2005): 4022-4028.
McNamara et al, Cell type specific delivery of siRNAs with aptamer-siRNA chimeras, *Nature Biotechnolgy*, 2006; 24: 1005-1015.
Gomez-Hens et al., "Long wavelength fluorophores: new trends in their analytical use," *Trends in Analytical Chemistry*, 2004; 23:127-136.
Definition of ligand, Random House Kernerman Webster's College Dictionary, downloaded on Jan. 25, 2014 from http://www.thefreedictionary.com/ligand, 1 page.
Eder et al., 68Ga-complex lipophilicity and the targeting property of a urea-based PSMA inhibitor for PET imaging, *Bioconjugate Chemistry*, 2012; 23:688-697.
Pubchem, Compound summary for: CID 58099954, Aug. 19, 2012.
Peltier et al., "The Total Synthesis of Tubulysin D," J. Am. Chem. Soc. 128:16018-19 (2006).
Pathak et al., Enzymic protecting group techniques in organic synthesis, Stereosel. Biocatal. 775-797 (2000).
Silverman, "The Organic Chemistry of Drug Design and Drug Action," Elsevier Academic Press (2nd Ed. 2003).
Larock, "Comprehensive Organic Transformations, a guide to functional group preparations," VCH Publishers, Inc. New York (1989). Table of Contents.
Theodora E. Greene & Peter G.M. Wuts, "Protective Groups ion Organic Synthesis," 2d edition, John Wiley & Sons, Inc. New York (1991). Table of Contents.
Vlahov, et al., "Design and regioselective synthesis of a new generation of targeted chemotherapeutics. Part 1: EC145, a folic acid conjugate of desacetylvinblastine monohydrazide," ScienceDirect, Bioorganic & Medical Chemistry Letters 16 (2006) 5093-5096.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
Roy, et al., "DUPA Conjugation of a Cytotoxic Indenoisoquinoline Topoisomerase I Inhibitor for Selective Prostate Cancer Cell Targeting," J. Med. Chem. 58 (2015) 3094-3103.
Kularatne, S., "Synthesis and Biological Analysis of Prostate-Specific Membrane Antigen-Targeted Anticancer Prodrugs," J. Med. Chem, 2010, 53(21), 7767-7777.
PCT International Search Report and Written Opinion for PCT/US2013/070007, dated Mar. 5, 2014.
Banerjee, S. et al., "Sequential SPECT and Optical Imaging of Experimental Models of Prostate Cancer with a Dual Modality Inhibitor of the Prostate-Specific Membrane Antigen," Angewandte Chemie International Edition, 2011, 50, 9167-9170.
Lu, G. et al., "Synthesis and SAR of $^{99m}$Tc/Re-labeled small molecule prostate specific membrane antigen inhibitors with novel polar chelates," Bioorganic and Medicinal Chemistry Letters, 2013, 23, 1557-1563.
Kaur, G. et al., "Biological evaluation of tubulysin A: a potential anticancer and antiangiogenic natural product," Biochem. J., 2006, 396, 235-242.
Bennett, V.J.," Analysis of fluorescently labeled substance P analogs: binding, imaging and receptor activation," BMC Chemical Biology, 2001, 1:1. doi:10.1186/1472-6769-1-1.
Banerjee, S.R. et al. "Synthesis and Evaluation of Technetium-99m- and Rhenium-Labeled Inhibitors of the Prostate-Specific Membrane Antigen (PSMA)," J Med Chem. Aug. 14, 2008; 51(15): 4501-4517.
Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.
Hillier, Shawn M., et al., "Preclinical Evaluation of Novel Glutamate-Urea-Lysine Analogues That Target Prostate-Specific Membrane Antigen as Molecular Imaging Pharmaceuticals for Prostate Cancer," Cancer Res. Sep. 1, 2009;69(17):6932-40.
Maresca, K. P., "A Series of Halogenated Heterodimeric Inhibitors of Prostate Specific Membrane Antigen (PSMA) as Radiolabeled Probes for Targeting Prostate Cancer," J. Med. Chem., 2009, 52 (2), pp. 347-357.
Maresca, K., et al., "Molecular targeting of prostate cancer with small molecule inhibitors of prostate specific membrane antigen (PSMA)," J. Nucl. Med. 2007, 48 (Supplement 2):25P.
Kularatne et al., "Prostate-specific membrane antigen targeted imaging and therapy of prostate cancer using a PSMA inhibitor as a homing ligand," *Molecular Pharmaceutics*, 6(3): 780-789 (2009).
Reddy et al., "PSMA-specific anti-tumor activity of the targeted-tubulysin conjugate, EC1169," *American Association for Cancer Research Annual Meeting* (Apr. 8, 2013) Poster.
Reddy et al., "PSMA-specific anti-tumor activity of the targeted-tubulysin conjugate, EC1169," *American Association for Cancer Research Annual Meeting* (Apr. 8, 2013) Presentation Abstract.
Wang et al., "Prostate-Specific Membrane Antigen Targeted Tubulysin Conjugates for Cancer Therapy," *246th ACS National Meeting and Exposition* (Sep. 8, 2013) Poster.
Cole et al., "Cancer theranostics: the rise of targeted magnetic nanoparticles," Trends in Biotechnology, 2011, 29, 323-332.
Radioisotopes in Medicine, from http://www.word-nuclear.org/information-library/non-power-nuclearapplications/radioisotopes-research/radioisotopes-in-medicine.aspx, Dec. 28, 2016, pp. 1-20.
J.M. Silvola et al., "Al$^{18}$F-NOTA-Folate Accumulates in Atherosclerotic Plaques and Can be Detected by PET/CT", Poster presented Nov. 7, 2015 in Orlando, FL at the 2015 American Heart Association, ReSuscitation Science Symposium (http://newsroom_heart.org/events/scientific-sessions-2015-newsroom- 2942760).

(56) References Cited

OTHER PUBLICATIONS

J.M. Silvola et al., "Al$^{18}$F-NOTA-Folate Accumulates in Atherosclerotic Plaques and Can be Detected by PET/CT", Published reference of poster, Nov. 10, 2015, at http://circ.ahajournals.org/content/132/Suppl_3/A18873?cited-by=&legid=circulationaha;132/Suppl_3/A18873; Circulation, 2015, 132:A18873.
Benesova, M. et al., "Linker Modifications of DOTA-conjugated Inhibitors of the Prostate-Specific Membrane Antigen (PSMA)," poster, presented at the European Association of Nuclear Medicine Conference on Oct. 21, 2013.
Benesova, M. et al., "Linker Modifications of DOTA-conjugated Inhibitors of the Prostate-Specific Membrane Antigen (PSMA)," abstract, Eur. J. Nucl. Med. Mol. Imaging, available Oct. 16, 2013, 40, Suppl. 2, S193.
Rinnab, L.; et al., "Evaluation of [$^{11}$C]-choline positron-emission/computed tomography in patients with increasing prostate-specific antigen levels after primary treatment for prostate cancer," *BJU Int*, 2007, 100, 786,793.
Reske, S.N.; et al., "Imaging Prostate Cancer with $^{11}$C-Choline PET/CT," J Nucl Med, 2006, 47, 1249-1254.
Zophel, K.; Kotzerke, J, "Is $^{11}$C-choline the most appropriate tracer for prostate cancer?" *Eur J Nucl Med Mol Imaging*, 2004, 31, 756-759.
Vees, H.; et al., "$^{18}$F-choline and/or $^{11}$C-acetate positron emission tomography: detection of residual or progressive subclinical disease at very low prostate-specific antigen values (<1 ng/mL) after radical prostatectomy," *BJU Int*, 2007, 99, 1415-1420.
Larson, S. M.; et al., "Tumor Localization of 16β$^{18}$F-Fluoro-5α-Dihydrotestosterone Versus $^{18}$F-FDG in Patients with Progressive, Metastatic Prostate Cancer," *J Nucl Med*, 2004, 45, 366-373.
Schuster, D.M.; et al., "Initial Experience with the Radiotracer Anti-1-Amino-3-$^{18}$F-Fluorocyclobutane-1-Carboxylic Acid with PET/CT in Prostate Carcinoma," *J Nucl Med*, 2007, 48, 56-63.
Tehrani, O.S.; et al., "Tumor Imaging Using 1-(2'-deoxy-2'-$^{18}$F-Fluoroβ-D-Arabinofuranosyl)Thymine and PET," *J Nuc/ Med*, 2007, 48, 1436-1441.
Mease RC. et al., "N-[N-[(S)-1,3-Dicarboxypropyl]Carbamoyl]-4-[$^{18}$F]Fluorobenzyl-LCysteine, [$^{18}$F]DCFBC: A New Imaging Probe for Prostate Cancer," Clin Cancer Res., 2008, 14, 3036-3043.
Zhou, J.; et al., "NAAG Peptidase Inhibitors and Their Potential for Diagnosis and Therapy," *Nat Rev Drug Discovery*, 2005, 4, 1015-1026.
Schulke, N.; et al., "The homodimer of prostate-specific membrane antigen is a functional target for cancer therapy," Proc Natl Acad Sci U S A, 2003, 100, 12590-12595.
Nan, F.; et al., "Dual Function Glutamate-Related Ligands: Discovery of a Novel, Potent Inhibitor of Glutamate Carboxypeptidase II Possessing mGluR3 Agonist Activity," J Med Chem, 2000, 43, 772-774.
Lange, P.H., "ProstaScint scan for staging prostate cancer," *Urology*, 2001, 57, 402-406.
Haseman, M.K.; et al., "Capromab Pendetide Imaging of Prostate Cancer," *Cancer Biother Radiopharm*, 2000, 15, 131-140.
Mier W., et al., "Conjugation of DOTA Using Isolated Phenolic Active Esters: The Labeling and Biodistribution of Albumin as Blood Pool Marker," *Bioconjugate Chem.*, 2005, 16: 237-240.
Schafer et al., "A dimerized urea-based inhibitor of the prostate-specific membrane antigen for $^{68}$Ga-PET imaging of prostate cancer," EJNMMI Research, 2012, 2, 23, 11 pages.
Humblet, V. et al., "An HPLC/mass spectrometry platform for the development of multimodality contrast agents and targeted therapeutics: prostate-specific membrane antigen small molecule derivatives," Contrast Med. Mol. Imaging, 2006, 1, 196-211.
Pomper, M.G.; et al., "$^{11}$C-MCG: synthesis, uptake selectivity, and primate PET of a probe for glutamate carboxypeptidase II (NAALADase)," Mol Imaging, 2002, 1, 96-101.
Scher, B.; et al., "Value of 11C-choline PET and PET/CT in patients with suspected prostate cancer," Eur. J. Nucl. Med. Mol. Imaging., 2007, 34, 45-53.

Tasch, J.; et al., "A Unique Folate Hydrolase, Prostage-Specific Membrane Antingen (PSMA): A Target for Immunotherapy?" Crit. Rev. lmmunol., 2001, 21, 249-261.
Rosenthal, S.A.; et al., "Utility of Capromab Pendetide (ProstaScint) Imaging in the Management of Prostate Cancer," Tech Urol, 2001, 7, 27-37.
Wiberg et al. A comparison of some properties of C=O and C=S bonds. ARKIVOC, 2011, pp. 45-56 (2011).
European Patent Application No. EP 14861854, by Endocyte, Inc. et al.: Partial Supplementary Search Report with Opinion; dated May 19, 2017 (15 pages).
European search report in EP 18175078, completed Sep. 6, 2018.
Chinese Patent Application No. 201480071256, by Endocyte, Inc. et al.: Office Action, dated Apr. 20, 2017 (9 pages).
Eurasian Patent Application No. 201690862/28, by Endocyte, Inc. et al.: Office Action, dated May 22, 2017; English Translation (2 pages).
Liu M., et al., "Synthesis and Biological Evaluation of Diethylenetriamine Pentaacetic acid-Polyethylene Glycol Folate: A new Folate-Derived, $^{99m}$Tc-Based Radiopharmaceutical," Bioconjugate Chem., 2005.
Muller C., et al. "Synthesis and in Vitro/in Vivo Evaluation of Novel $^{99m}$Tc(CO)$_3$-Folates," Bioconjugate Chem., 2006 vol. 17, p. 797-806.
Viola-Villegas N., et al. "Targeting Gallium to Cancer Cells through the Folate Receptor," Drug Target Insights, 2008 vol. 3, p. 13-25.
Viola-Villegas N., et al. "Targeting the Folate Receptor (FR): Imaging and Cytotoxicity of Re$^I$ Conjugates in FR-Overexpressing Cancer Cells," ChemMedChem, 2008 vol. 3, p. 1387-1394.
Zhou J., "In vivo evaluation of medical device-associated inflammation using macrophage-specific position emission tomography (PET) imaging," Bioorganic and Medicinal Chemistry Letters, 2013 vol. 23, p. 2044-2047.
Kularatne SA., et al. "Comparative Analysis of Folate Derived PET Imaging Agents with [$^{18}$F]-2-Fluoro-2-deoxy-D-glucose Using Rodent Inflammatory Paw Model," Molecular Pharmaceutics, 2013 vol. 10, p. 3103-3111.
Kothari et al., "$^{18}$F-labeled small molecule inhibitors of prostate specific membrane antigen (PSMA) for PET imaging of prostate cancer," J Nucl Med May 2012 vol. 53 No. supplement 1 1721.
Hillier et al., "[$^{131}$I] MIP-1466, a small molecule prostate-specific membrane antigen (PSMA) inhibitor for targeted radiotherapy of prostate cancer (PCa)," J Nucl Med May 2012 vol. 53 No. supplement 1 170.
Armor et al., "A comparison of 2D and 3D regions within the same patient to derive organ and tissue kinetics," J Nucl Med May 2012 vol. 53 No. supplement 1 13.
Afshar-Oromieh et al., "[$^{68}$Ga]Gallium-labelled PSMA ligand as superior PET tracer for the diagnosis of prostate cancer: comparison with $^{18}$F-FECH," Eur J Nucl Med Mol Imaging (2012) 39:1085-1086.
Afshar-Oromieh et al., "Comparison of PET/CT and PET/MRI hybrid systems using a $^{68}$Ga-labelled PSMA ligand for the diagnosis of recurrent prostate cancer: initial experience," Eur J Nucl Med Mol Imaging (2014) 41:887-897.
Afshar-Oromieh et al., "Comparison of PET imaging with a $^{68}$Ga-labelled PSMA ligand and $^{18}$F-choline-based PET/CT for the diagnosis of recurrent prostate cancer," Eur J Nucl Med Mol Imaging (2014) 41:11-20.
Afshar-Oromieh et al., "PET/MRI with a $^{68}$Ga-PSMA ligand for the detection of prostate cancer," Eur J Nucl Med Mol Imaging (2013) 40:1629-1630.
Afshar-Oromieh et al., "PET imaging with a [$^{68}$Ga]gallium-labelled PSMA ligand for the diagnosis of prostate cancer: biodistribution in humans and first evaluation of tumour lesions," Eur J Nucl Med Mol Imaging (2013).
Afshar-Oromieh et al., "The diagnostic value of PET/CT imaging with the 68Ga-labelled PSMA ligand HBED-CC in the diagnosis of recurrent prostate cancer," Eur J Nucl Med Mol Imaging (2015) 42:197-209.
Aggarwal et al., "A Dimeric Peptide That Binds Selectively to Prostate-Specific Membrane Antigen and Inhibits its Enzymatic Activity," Cancer Res 2006; 66: 9171-9177, Sep. 15, 2006.

(56) References Cited

OTHER PUBLICATIONS

Alt et al., "High-Resolution Animal PET Imaging of Prostate Cancer Xenografts with Three Different [68]Cu-Labeled Antibodies against Native Cell-Adherent PSMA," The Prostate 70:1413-1421 (2010).
Ananias et al., "Expression of the Gastrin-Releasing Peptide Receptor, the Prostate Stem Cell Antigen and the Prostate-Specific Membrane Antigen in Lymph Node and Bone Metastases of Prostate Cancer," The Prostate 69:1101-1108 (2009).
Anderson et al., "Substrate specificity of prostate-specific membrane antigen," Bioorganic & Medicinal Chemistry 15 (2007) 6678-6686.
Antunes et al., "PGC and PSMA in prostate cancer diagnosis: tissue analysis from biopsy samples," Int Braz J Urol. 2013; 39: 649-56.
Bacich et al., "Cloning, expression, genomic localization, and enzymatic activities of the mouse homolog of prostate-specific membrane antigen/NAALADase/folate hydrolase," Mammalian Genome 12, 117-123 (2001).
Baiz et al., "Synthesis and Characterization of a Novel Prostate Cancer-Targeted Phosphatidylinositol-3-kinase Inhibitor Prodrug," J. Med. Chem. 2012, 55, 8038-8046.
Banerjee et al., "[64]Cu-Labeled Inhibitors of Prostate-Specific Membrane Antigen for PET Imaging of Prostate Cancer," J. Med. Chem. 2014, 57, 2657-2669.
Banerjee et al., "[68]Ga-Labeled Inhibitors of Prostate-Specific Membrane Antigen (PSMA) for Imaging Prostate Cancer," J. Med. Chem. 2010, 53, 5333-5341.
Banerjee et al., "A Modular Strategy to Prepare Multivalent Inhibitors of Prostate-Specific Membrane Antigen (PSMA)," Oncotarget 2011; vol. 2, No. 12, 1244-1253.
Banerjee et al., "Effect of Chelators on the Pharmacokinetics of [99m]Tc-Labeled Imaging Agents for the Prostate-Specific Membrane Antigen (PSMA)," J. Med. Chem. 2013, 56, 6108-6121.
Barinka et al., "A high-resolution structure of ligand-free human glutamate carboxypeptidase II," Acta Cryst. (2007). F63, 150-153.
Barinka et al., "Interactions between Human Glutamate Carboxypeptidase II and Urea-Based Inhibitors: Structural Characterization," J. Med. Chem. 2008, 51, 7737-7743.
Barinka et al., "Structural Insight into the Pharmacophore Pocket of Human Glutamate Carboxypeptidase II," J. Med. Chem. 2007, 50, 3267-3273.
Barrett et al., "First-in-Man Evaluation of 2 High-Affinity PSMA-Avid Small Molecules for Imaging Prostate Cancer," J Nucl Med. 2013;54:380-387.
Belloli et al., "Characterization of preclinical models of prostate cancer using PET-based molecular imaging," Eur J Nucl Med Mol Imaging (2009) 36:1245-1255.
Bostwick et al., "Prostate Specific Membrane Antigen Expression in Prostatic Intraepithelial Neoplasia and Adenocarcinoma," Cancer 1998;82:2256-61.
Bouchelouche et al., "Imaging Prostate Cancer: An Update on Positron Emission Tomography and Magnetic Resonance Imaging," Curr Urol Rep (2010) 11:180-190.
Bouchelouche et al., "Prostate Specific Membrane Antigen—A Target for Imaging and Therapy with Radionuclides," Discov Med. Jan. 2010 ; 9(44): 55-61.
Bzdega et al., "The cloning and characterization of a second brain enzyme with NAAG peptidase activity," Journal of Neurochemistry, 2004, 89, 627-635.
Ceci et al., "[11]C-Choline PET/CT in patients with hormone-resistant prostate cancer showing biochemical relapse after radical prostatectomy," Eur J Nucl Med Mol Imaging (2013) 40:149-155.
Chang et al., "Five Different Anti-Prostate-specific Membrane Antigen (PSMA) Antibodies Confirm PSMA Expression in Tumor-associated Neovasculature," Cancer Research 59, 3192-3198, Jul. 1, 1999.
Chang et al., "The clinical role of prostate-specific membrane antigen (PSMA)," Urologic Oncology 7 (2002) 7-12.

Chen et al., "A low molecular weight PSMA-based fluorescent imaging agent for cancer," Biochemical and Biophysical Research Communications 390 (2009) 624-629.
Chen et al., "PSMA-Targeted Theranostic Nanoplex for Prostate Cancer Therapy," ACS Nano 2012, vol. 6, No. 9, 7752-7762.
Chen et al., "Synthesis and Biological Evaluation of Low Molecular Weight Fluorescent Imaging Agents for the Prostate-Specific Membrane Antigen," Bioconjugate Chem. 2012, 23, 2377-2385.
Chopra A., "[68]Ga-Labeled 2-[3-(1-carboxy-5-{7-[5-carboxy-5-(3-phenyl-2- {3- phenyl-2-[2-(4,7,10-tris-carboxymethyl- 1,4,7,10-tetraazacyclododec-1-1)acetylamino]propionylamino}propionylamino)pentylcarbamoyl]heptanoylamino}pentyl)ureido]pentanedioic acid," Sep. 27, 2010 [Updated Dec. 28, 2010]. In: Molecular Imaging and Contrast Agent Database (MICAD) [Internet]. Bethesda (MD): National Center for Biotechnology Information (US); 2004-2013.
Chopra A, "[68]Ga-Labeled 2- {3-[5-(7-{1-benzyloxycarbonyl-5-[2-(4,7,10-triscarboxymethyl-1,4,7,10-tetraazacyclododec-1-1)acetylamino]pentylcarbamoyl}-heptanoylamino)-1-carboxypentyl]ureido }pentanedioic acid," Sep. 28, 2010 [Updated Dec. 28, 2010]. In: Molecular Imaging and Contrast Agent Database (MICAD) [Internet]. Bethesda (MD): National Center for Biotechnology Information (US); 2004-2013.
Chuu et al., "Androgen suppresses proliferation of castrationresistant LNCaP 104-R2 prostate cancer cells through androgen receptor, Skp2, and c-Myc," Cancer Sci 2011; 102: 2022-2028.
Cimitan et al., "[18F]fluorocholine PET/CT imaging for the detection of recurrent prostate cancer at PSA relapse: experience in 100 consecutive patients," Eur J Nucl Med Mol Imaging (2006) 33:1387-1398.
Colabufo et al., "PB183, a sigma receptor ligand, as a potential PET probe for the imaging of prostate adenocarcinoma," Bioorganic & Medicinal Chemistry Letters 18 (2008) 1990-1993.
Cunha et al., "Tissue-specificity of prostate specific antigens: Comparative analysis of transcript levels in prostate and non-prostatic tissues," Cancer Letters 236 (2006) 229-238.
Dahl et al., "Sarcosine induces increase in HER2/neu expression in androgen-dependent prostate cancer cells," Mol Biol Rep (2011) 38:4237-4243.
DeGrado et al., "Synthesis and Evaluation of 18F-Labeled Choline Analogs as Oncologic PET Tracers," J Nucl Med 2001; 42:1805-1814.
DeGrado et al., "Synthesis and Evaluation of 18F-labeled Choline as an Oncologic Tracer for Positron Emission Tomography: Initial Findings in Prostate Cancer," Cancer Research 61, 110-117, Jan. 1, 2000.
De Santis et al., "Rolle der Chemotherapie beim kastrationsresistenten Prostatakarzinom," Urologe 2012 • 51:39-43.
Dimitrakopoulou-Strauss et al., "PET Imaging of Prostate Cancer with [11]C-Acetate," Nucl Med. 2003;44:556-558.
Dumas et al., "Molecular Expression of PSMA mRNA and Protein in Primary Renal Tumors," Int. J. Cancer: 80, 799-803 (1999).
Eder et al., "Pharmacokinetic Properties of Peptidic Radiopharmaceuticals: Reduced Uptake of (EH)3-Conjugates in Important Organs," Nucl Med 2013; 54:1-4.
Eder et al., "Novel Preclinical and Radiopharmaceutical Aspects of [68Ga]Ga-PSMA-HBED-CC: A New PET Tracer for Imaging of Prostate Cancer," Pharmaceuticals 2014, 7, 779-796.
Eder et al., "Preclinical Evaluation of a Bispecific Low-Molecular HeterodimerTargeting Both PSMA and GRPR for Improved PET Imaging and Therapy of Prostate Cancer," The Prostate 74:659-668 (2014).
Eder et al., "PSMA as a target for radiolabelled small molecules," Eur J Nucl Med Mol Imaging (2013) 40:819-823.
Eiber et al., "[68]Ga-PSMA PET/MR with multimodality image analysis for primary prostate cancer," Abdom Imaging (2015) 40:1769-1771.
Elsasser-Beile et al., "PET Imaging of Prostate Cancer Xenografts with a Highly Specific Antibody against the Prostate-Specific Membrane Antigen," J Nucl Med 2009; 50:606-611.
Elsasser-Beile et al., "Targeted Therapies for Prostate Cancer Against the Prostate Specific Membrane Antigen," Current Drug Targets, 2009, 10, 118-125.

(56) References Cited

OTHER PUBLICATIONS

Elsasser-Beile et al., "A New Generation of Monoclonal and Recombinant Antibodies Against Cell-Adherent Prostate Specific Membrane Antigen for Diagnostic and Therapeutic Targeting of Prostate Cancer," The Prostate 66:1359-1370 (2006).
El-Zaria et al., "Preparation and evaluation of carborane-derived inhibitors of prostate specific membrane antigen (PSMA)," Dalton Trans., 2014, 43, 4950-4961.
Emonds et al., "Do androgens control the uptake of $^{18}$F-FDG, $^{11}$C-choline and $^{11}$C-acetate in human prostate cancer cell lines?," Eur J Nucl Med Mol Imaging (2011) 38:1842-1853.
Eur J Nucl Med Mol Imaging (2012) 39 (Suppl 2):S304-S353. ISTARD Posters.
Evans et al., "Noninvasive measurement of androgen receptor signaling with a positron-emitting radiopharmaceutical that targets prostate-specific membrane antigen," PNAS, vol. 108, No. 23, 9578-9582, Jun. 7, 2011.
Fair et al., "Prostate-Specific Membrane Antigen," The Prostate 32:140-148 (1997).
Fall et al., "Prostate-Specific Antigen Levels as a Predictor of Lethal Prostate Cancer," J Natl Cancer Inst 2007;99: 526-32.
Fortmuller et al., "Effective Targeting of Prostate Cancer by Lymphocytes Redirected by a PSMA × CD3 Bispecific Single-Chain Diabody," The Prostate 71:588-596 (2011).
Fortuin et al., "Value of PET/CT and MR Lymphography in Treatment of Prostate Cancer Patients With Lymph Node Metastases," Int J Radiation Oncol Biol Phys, vol. 84, No. 3, pp. 712e718, 2012.
Foss et al., "GCPII Imaging and Cancer," Current Medicinal Chemistry, 2012, 19, 1346-1359.
Franc et al., "Detection and localization of carcinoma within the prostate using high resolution transrectal gamma imaging (TRGI) of monoclonal antibody directed at prostate specific membrane antigen (PSMA)—Proof of concept and initial imaging results," European Journal of Radiology 82 (2013) 1877-1884.
Frigerio et al., "A single-chain fragment against prostate specific membrane antigen as a tool to build theranostic reagents for prostate cancer," European Journal of Cancer (2013) 49, 2223-2232.
Ghosh et al., "Tumor Target Prostate Specific Membrane Antigen (PSMA) and its Regulation in Prostate Cancer," Journal of Cellular Biochemistry 91:528-539 (2004).
Giovacchini et al., "Predictive factors of [$^{11}$C]choline PET/CT in patients with biochemical failure after radical prostatectomy," Eur J Nucl Med Mol Imaging (2010) 37:301-309.
Goodman Jr. et al., "Interaction of prostate specific membrane antigen with clathrin and the adaptor protein complex-2," International Journal of Oncology 31: 1199-1203, 2007.
Graham et al., "Radiofluorinated Derivatives of 2-(Phosphonomethyl)pentanedioic Acid as Inhibitors of Prostate Specific Membrane Antigen (PSMA) for the Imaging of Prostate Cancer," J. Med. Chem. 2012, 55, 9510-9520.
Gregor et al., "Induction of autoantibodies to syngeneic prostate-specific membrane antigen by xenogeneic vaccination," Int. J. Cancer: 116, 415-421 (2005).
Haberkorn et al., "Mechanistic and high-throughput approaches for the design of molecular imaging probes and targeted therapeutics," Clin Transl Imaging (2014) 2:33-41.
Haffner et al., "Prostate-specific membrane antigen expression in the neovasculature of gastric and colorectal cancers," Human Pathology (2009) 40, 1754-1761.
Hara, Toshihiko, "$^{11}$C-Choline and 2-Deoxy-2- [$^{18}$F]Fluoro-D-Glucose in Tumor Imaging with Positron Emission Tomography," Molecular Imaging and Biology, 2002, vol. 4, No. 4, 267-273.
Harada et al., "Preparation of Asymmetric Urea Derivatives that Target Prostate-Specific Membrane Antigen for SPECT Imaging," J. Med. Chem. 2013, 56, 7890-7901.
Heidenreich, A., "Immuntherapie beim metastasierten Prostatakarzinom—brauchen wir diese wirklich?," Urologe 2012 • 51:32-38.

Hillier et al., "123I-MIP-1072, a Small-Molecule Inhibitor of Prostate-Specific Membrane Antigen, Is Effective at Monitoring Tumor Response to Taxane Therapy," J Nucl Med 2011; 52:1087-1093.
Hillier et al., "99mTc-Labeled Small-Molecule Inhibitors of Prostate-Specific Membrane Antigen for Molecular Imaging of Prostate Cancer," J Nucl Med 2013; 54:1369-1376.
Hlouchova et al., "Biochemical characterization of human glutamate carboxypeptidase III," Journal of Neurochemistry, 2007, 101, 682-696.
Hlouchova et al., "GCPII Variants, Paralogs and Orthologs," Current Medicinal Chemistry, 2012, 19, 1316-1322.
Hlouchova et al., "Structural insight into the evolutionary and pharmacologic homology of glutamate carboxypeptidases II and III," FEBS Journal 276 (2009) 4448-4462.
Ho et al., "Molecular Imaging, Pharmacokinetics, and Dosimetry of $^{111}$In-AMBA in Human Prostate Tumor-Bearing Mice," Journal of Biomedicine and Biotechnology vol. 2011, Article ID 101497, 8 pages.
Holland et al., "$^{89}$Zr-DFO-J591 for ImmunoPET of Prostate-Specific Membrane Antigen Expression In Vivo," J Nucl Med 2010; 51:1293-1300.
Hong et al., "Positron emission tomography imaging of prostate cancer," Amino Acids (2010) 39:11-27.
Hospers et al., "PET Imaging of Steroid Receptor Expression in Breast and Prostate Cancer," Current Pharmaceutical Design, 2008, 14, 3020-3032.
Huang et al., "Improving the Biodistribution of PSMA-Targeting Tracers With Highly Negatively Charged Linker," The Prostate 74:702-713 (2014).
Huang et al., "PSMA-Targeted Stably Linked 'Dendrimer-Glutamate Urea-Methotrexate' as a Prostate Cancer Therapeutic," Biomacromolecules 2014, 15, 915-923.
Humblet et al., "High-affinity Near-infrared Fluorescent Small-molecule Contrast Agents for In Vivo Imaging of Prostate-specific Membrane Antigen," Molecular Imaging . vol. 4, No. 4, Oct. 2005, pp. 448-462.
Humblet et al., "Multivalent Scaffolds for Affinity Maturation of Small Molecule Cell Surface Binders and Their Application to Prostate Tumor Targeting," J. Med. Chem. 2009, 52, 544-550.
Husarik et al., "Evaluation of [$^{18}$F]-choline PET/CT for staging and restaging of prostate cancer," Eur J Nucl Med Mol Imaging (2008) 35:253-263.
Hwang et al., "Imaging Prostate Derived Tumors with PET and N-(3- [$^{18}$F]Fluoropropyl)putrescine," Nucl. Med. Biol. vol. 17, No. 6, pp. 525-532, 1990.
Hwang et al., "N-3- [$^{18}$F]Fluoropropylputrescine as Potential PET Imaging Agent for Prostate and Prostate Derived Tumors," J Nucl Med 30:1205-1210, 1989.
Igerc et al., "The value of $^{18}$F-Choline PET/CT in patients with elevated PSA-level and negative prostate needle biopsy for localisation of prostate cancer," Eur J Nucl Med Mol Imaging (2008) 35:976-983.
Jackson et al., "Design, Synthesis, and Biological Activity of a Potent Inhibitor of the Neuropeptidase N-Acetylated α-Linked Acidic Dipeptidase," J. Med. Chem. 1996, 39, 619-622.
Jadvar et al., "Glucose Metabolism of Human Prostate Cancer Mouse Xenografts," Molecular Imaging, vol. 4, No. 2, Apr. 2005, pp. 91-97.
Jadvar et al., "Imaging evaluation of prostate cancer with $^{18}$F-fluorodeoxyglucose PET/CT: utility and limitations," Eur J Nucl Med Mol Imaging (2013) 40 (Suppl 1):S5-S10.
Jadvar et al., "Molecular Imaging of Prostate Cancer: PET Radiotracers," AJR 2012; 199:278-291.
Jadvar et al., "Molecular imaging of prostate cancer with $^{18}$F-fluorodeoxyglucose PET," Nat. Rev. Urol. 6, 317-323 (2009).
Jambor et al., "Functional Imaging of Localized Prostate Cancer Aggressiveness Using $^{11}$C-Acetate PET/CT and $^{1}$H-MR Spectroscopy," J Nucl Med 2010; 51:1676-1683.
Jemaa et al., "A Comparison of the Biological Features of Prostate Cancer with (PSA+, PSMA+) Profile according to RKIP," BioMed Research International vol. 2013, Article ID 409179, 7 pages.

(56) References Cited

OTHER PUBLICATIONS

Jemaa et al., "A novel regulation of PSMA and PSA expression by Q640X AR in 22Rv1 and LNCaP prostate cancer cells," Cell Biol Int 37 (2013) 464-470.

Jemaa et al., "Cellular distribution and heterogeneity of PSA and PSMA expression in normal, hyperplasia and human prostate cancer," La Tunisie Medicale—2013 ; vol. 91 (n°07) : 458-463.

Kahn et al., "[111]Indium-Capromab Pendetide in the Evaluation of Patients with Residual or Recurrent Prostate Cancer After Radical Prostatectomy," The Journal of Urology vol. 159, 2041-2047, Jun. 1998.

Kasten et al., "Targeting prostate cancer cells with PSMA inhibitor-guided gold nanoparticles," Bioorganic & Medicinal Chemistry Letters 23 (2013) 565-568.

Kim et al., "Tribody: Robust Self-Assembled Trimeric Targeting Ligands with High Stability and Significantly Improved Target-Binding Strength," Biochemistry 2013, 52, 7283-7294.

Kinoshita et al., "Expression of Prostate-Specific Membrane Antigen in Normal and Malignant Human Tissues," World J Surg (2006) 30: 628-636.

Klotz, Laurence, "Cancer overdiagnosis and overtreatment," Curr Opin Urol 2012, 22:203-209.

Klusak et al., "Reaction Mechanism of Glutamate Carboxypeptidase II Revealed by Mutagenesis, X-ray Crystallography, and Computational Methods," Biochemistry 2009, 48, 4126-4138.

Kosuri et al., "Review of Salvage Therapy for Biochemically Recurrent Prostate Cancer: The Role of Imaging and Rationale for Systemic Salvage Targeted Anti-Prostate-SpecificMembrane Antigen Radioimmunotherapy," Advances in Urology vol. 2012, Article ID 921674, 8 pages.

Kotzerke et al., "PET for Prostate Cancer Imaging: Still a Quandary or the Ultimate Solution?," The Journal of Nuclear Medicine, vol. 43, No. 2, Feb. 2002.

Kovar et al., "Pharmacokinetic and Biodistribution Assessment of a Near Infrared-Labeled PSMA-Specific Small Molecule in Tumor-Bearing Mice," Prostate Cancer vol. 2014, Article ID 104248, 10 pages.

Krohn et al., "[$^{68}$Ga]PSMA-HBED uptake mimicking lymph node metastasis in coeliac ganglia: an important pitfall in clinical practice," Eur J Nucl Med Mol Imaging (2015) 42:210-214.

Kuru et al., "MRT-navigierte stereotaktische Prostatabiopsie," Urologe 2012 • 51:50-56.

Kwee et al., "[$^{18}$F]-choline PET/CT imaging of RECIST measurable lesions in hormone refractory prostate cancer," Ann Nucl Med (2009) 23:541-548.

Lambert et al., "Molecular Evolution of the Transferrin Receptor/Glutamate Carboxypeptidase II Family," J Mol Evol (2007) 64:113-128.

Lapi et al., "Assessment of an 18F-Labeled Phosphoramidate Peptidomimetic as a New Prostate-Specific Membrane Antigen—Targeted Imaging Agent for Prostate Cancer," J Nucl Med 2009; 50:2042-2048.

Leek et al., "Prostate-specific membrane antigen: evidence for the existence of a second related human gene," British Journal of Cancer (1995) 72, 583-588.

Lees et al., "Active surveillance in prostate cancer: patient selection and triggers for intervention," Curr Opin Urol 2012, 22:210-215.

Lesche et al., "Preclinical evaluation of BAY 1075553, a novel $^{18}$F-labelled inhibitor of prostate-specific membrane antigen for PET imaging of prostate cancer, " Eur J Nucl Med Mol Imaging (2014) 41:89-101.

Liu et al., "C-11 Choline PET/CT Imaging for Differentiating Malignant From Benign Prostate Lesions," Clin Nucl Med 2008;33: 671-676.

Liu et al., "Constitutive and Antibody-induced Internalization of Prostate-specific Membrane Antigen," Cancer Research 58, 4055-4060, Sep. 15, 1998.

Liu et al., "Functional prostate-specific membrane antigen is enriched in exosomes from prostate cancer cells," International Journal of Oncology 44: 918-922, 2014.

Liu et al., "Prolonged androgen deprivation leads to downregulation of androgen receptor and prostate-specific membrane antigen in prostate cancer cells," International Journal of Oncology 41: 2087-2092, 2012.

Liu et al., "Pseudoirreversible Inhibition of Prostate-Specific Membrane Antigen by Phosphoramidate Peptidomimetics," Biochemistry 2008, 47, 12658-12660.

Liu et al., "Targeting prostate cancer cells with a multivalent PSMA inhibitor-guided streptavidin conjugate," Bioorganic & Medicinal Chemistry Letters 22 (2012) 3931-3934.

Lord et al., "$^{18}$F-Fluorocholine integrated PET/MRI for the initial staging of prostate cancer," Eur J Nucl Med Mol Imaging (2011) 38:2288.

Liu et al., "A targeted low molecular weight near-infrared fluorescent probe for prostate cancer," Bioorganic & Medicinal Chemistry Letters 20 (2010) 7124-7126.

Luboldt et al., "Prostate Carcinoma: Diffusion-weighted Imaging as Potential Alternative to Conventional MR and $^{11}$C-Choline PET/CT for Detection of Bone Metastases," Radiology: vol. 249: No. 3—Dec. 2008.

Lutje et al., "Dual-Modality Image-Guided Surgery of Prostate Cancer with a Radiolabeled Fluorescent Anti-PSMA Monoclonal Antibody," J Nucl Med 2014; 55:995-1001.

Lutje et al., "Prospects in Radionuclide Imaging of Prostate Cancer," The Prostate 72:1262-1272 (2012).

Malik et al., "One pot radiofluorination of a new potential PSMA ligand [Al $^{18}$F]NOTA-DUPA-Pep," J. Label Compd. Radiopharm 2012, 55 320-325.

Malik et al., "Radiosynthesis of a new PSMA targeting ligand ([$^{18}$F]FPy-DUPA-Pep)," Applied Radiation and Isotopes 69 (2011) 1014-1018.

Mannweiler et al., "Heterogeneity of Prostate-Specific Membrane Antigen (PSMA) Expression in Prostate Carcinoma with Distant Metastasis," Pathol. Oncol. Res. (2009) 15:167-172.

Maresca et al., "Influence of functionalized chelators on affinity and pharmacokinetics of $^{99m}$Tc(CO)$_3$-labeled small molecules targeting prostate specific membrane antigen (PSMA)," J Nucl Med May 2010 vol. 51 No. supplement 2 250.

Matthies et al., "Imaging of prostate cancer metastases with $^{18}$F-fluoroacetate using PET/CT," Eur J Nucl Med Mol Imaging (2004) 31:797.

Mease et al., "PET Imaging in Prostate Cancer: Focus on Prostate-Specific Membrane Antigen," Current Topics in Medicinal Chemistry, 2013, 13, 951-962.

Meighan et al., "Recombinant Glutamate Carboxypeptidase II (Prostate Specific Membrane Antigen—PSMA)—Cellular Localization and Bioactivity Analyses," Journal of Protein Chemistry, vol. 22, No. 4, May 2003.

Meinhardt et al., "Laparoscopic Sentinel Lymph Node Biopsy for Prostate Cancer: The Relevance of Locations Outside the Extended Dissection Area," Prostate Cancer vol. 2012, Article ID 751753, 4 pages.

Mertens et al., "PET with $^{18}$F-labelled choline-based tracers for tumour imaging: a review of the literature," Eur J Nucl Med Mol Imaging (2010) 37:2188-2193.

Mhawech-Fauceglia et al., "Prostate-specific membrane antigen (PSMA) protein expression in normal and neoplastic tissues and its sensitivity and specificity in prostate adenocarcinoma: an immunohistochemical study using mutiple tumour tissue microarray technique," Histopathology 2007, 50, 472-483.

Minner et al., "High Level PSMA Expression Is Associated With Early PSA Recurrence in Surgically Treated Prostate Cancer," The Prostate 71:281-288 (2011).

Mlcochova et al., "Mapping of the active site of glutamate carboxypeptidase II by site-directed mutagenesis," FEBS Journal 274 (2007) 4731-4741.

Moltzahn et al., "Die ossäre Metastasierung des Prostatakarzinoms," Urologe 2012 • 51:20-26.

Morris et al., "$^{11}$C-acetate PET imaging in prostate cancer," Eur J Nucl Med Mol Imaging (2007) 34:181-184.

Murphy et al., "Current Evaluation of the Tissue Localization and Diagnostic Utility of Prostate Specific Membrane Antigen," Cancer 1998;83:2259-69.

(56) References Cited

OTHER PUBLICATIONS

Nedrow-Byers et al., "A Phosphoramidate-Based Prostate-Specific Membrane Antigen-Targeted SPECT Agent," The Prostate 72:904-912 (2012).
Office Action (English translation) in Chinese Patent Application No. 201610184873, dated Jul. 24, 2018 (6 pages).
O'Keefe et al., "Comparative Analysis of Prostate-Specific Membrane Antigen (PSMA) Versus a Prostate-Specific Membrane Antigen-Like Gene," The Prostate 58:200-210 (2004).
Omlin et al., "Androgen- und Östrogen-biosynthesehemmer beim kastrationsresistenten Prostatakarzinom," Urologe 2012 • 51:8-14.
Osborne et al., "A Prospective Pilot Study of 89Zr-J591/Prostate Specific Membrane Antigen Positron Emission Tomography in Men with Localized Prostate Cancer Undergoing Radical Prostatectomy," The Journal of Urology, vol. 191, 1439-1445, May 2014.
Oyama et al., "$^{11}$C-Acetate PET Imaging of Prostate Cancer," J Nucl Med 2002; 43:181-186.
Oyama et al., "$^{11}$C-Acetate PET Imaging of Prostate Cancer: Detection of Recurrent Disease at PSA Relapse," J Nucl Med 2003; 44:549-555.
Oyama et al., "PET Imaging in Prostate Cancer," Hinyokika Kiyo 52: 503-505, 2006.
Office Action in European Patent Application No. 2014002808, dated Sep. 7, 2018 (3 pages).
Parker et al., "Design, production, and characterization of a single-chain variable fragment (ScFv) derived from the prostate specific membrane antigen (PSMA) monoclonal antibody J591," Protein Expression and Purification 89 (2013) 136-145.
Pavlicek et al., Glutamate Carboxypeptidase II: An Overview of Structural Studies and Their Importance for Structure-Based Drug Design and Deciphering the Reaction Mechanism of the Enzyme, Current Medicinal Chemistry, 2012, 19, 1300-1309.
Pavlicek et al., "Structural characterization of P1'-diversified urea-based inhibitors of glutamate carboxypeptidase II," Bioorganic & Medicinal Chemistry Letters 24 (2014) 2340-2345.
Perner et al., "Prostate-specific membrane antigen expression as a predictor of prostate cancer progression," Human Pathology (2007) 38, 696-701.
Pillarsetty et al., "2-$^{18}$F-Fluoropropionic Acid as a PET Imaging Agent for Prostate Cancer," J Nucl Med 2009; 50:1709-1714.
Pinto et al., "Imaging in Prostate Cancer Staging: Present Role and Future Perspectives," Urol Int 2012;88:125-136.
Ponde et al., "$^{18}$F-Fluoroacetate: A Potential Acetate Analog for Prostate Tumor Imaging—In Vivo Evaluation of $^{18}$F-Fluoroacetate Versus $^{11}$C-Acetate," J Nucl Med 2007; 48:420-428.
Preusser et al., "Kastrationsresistentes Prostatakarzinom," Urologe 2012 • 51:27-31.
Rais et al., "Bioanalytical method for evaluating the pharmacokinetics of the GCP-II inhibitor 2-phosphonomethylpentanedioicacid (2-PMPA)," Journal of Pharmaceutical and Biomedical Analysis 88 (2014) 162-169.
Rajasekaran et al., "A Novel Cytoplasmic Tail MXXXL Motif Mediates the Internalization of Prostate-specific Membrane Antigen," Molecular Biology of the Cell, vol. 14, 4835-4845, Dec. 2003.
Reske et al., "[$^{11}$C]choline PET/CT imaging in occult local relapse of prostate cancer after radical prostatectomy," Eur J Nucl Med Mol Imaging (2008) 35:9-17.
Reske et al., "[$^{11}$C]Choline uptake with PET/CT for the initial diagnosis of prostate cancer: relation to PSA levels, tumour stage and anti-androgenic therapy," Eur J Nucl Med Mol Imaging (2008) 35:1740-1741.
Reske et al., "Weiterentwicklung der PET und des PET/CT beim Prostatakarzinom," Urologe 2006 • 45:707-714.
Reske et al., "Nuklearmedizinische Diagnostik beim Prostatakarzinom," Urologe 2007 • 46:1485-1499.
Reske et al., "PET und PET/CT in der Rezidivdiagnostik des Prostatakarzinoms," Urologe 2006 • 45:1240-1250.
Rinnab et al., "[$^{11}$C]Choline PET/CT for Targeted Salvage Lymph Node Dissection in Patients with Biochemical Recurrence after Primary Curative Therapy for Prostate Cancer," Urol Int 2008;81:191-197.
Rinnab et al., "[$^{11}$C]choline PET/CT in prostate cancer patients with biochemical recurrence after radical prostatectomy," World J Urol (2009) 27:619-625.
Ristau et al., "The prostate-specific membrane antigen: Lessons and current clinical implications from 20 years of research," Urologic Oncology: Seminars and Original Investigations 32 (2014) 272-279.
Roethke et al., "Hyrbid Positron Emission Tomography-Magnetic Resonance Imaging with Gallium 68 Prostate-specific Membrane Antigen Tracer: A Next Step for Imaging of Recurrent Prostate Cancer—Preliminary Results," European Urology 64 (2013) 862-864.
Rybalov et al., "Impact of total PSA, PSA doubling time and PSA velocity on detection rates of $^{11}$C-Choline positron emission tomography in recurrent prostate cancer," World J Urol (2013) 31:319-323.
Sacha et al., "Expression of Glutamate Carboxypeptidase II in Human Brain," Neuroscience 144 (2007) 1361-1372.
Scattoni et al., "Detection of Lymph-Node Metastases with Integrated [11C]Choline PET/CT in Patients with PSA Failure after Radical Retropubic Prostatectomy: Results Confirmed by Open Pelvic-Retroperitoneal Lymphadenectomy," European Urology 52 (2007) 423-429.
Scheffel et al., "PET Imaging of GRP Receptor Expression in Prostate Cancer," The Journal of Nuclear Medicine, vol. 45, No. 8, Aug. 2004.
Scher et al., "PET/CT imaging of recurrent prostate cancer," Eur J Nucl Med Mol Imaging (2008) 35:5-8.
Shvarts et al., "Positron Emission Tomography in Urologic Oncology," Cancer Control, Jul./Aug. 2002, vol. 9, No. 4, 335-342.
Silver et al., "Prostate-specific Membrane Antigen Expression in Normal and Malignant Human Tissues," Clinical Cancer Research, vol. 3, 81-85, Jan. 1997.
Slusher et al., "Immunocytochemical Localization of the N-Acetyl-Aspartyl-Glutamate (NAAG) Hydrolyzing Enzyme N-Acetylated α-Linked Acidic Dipeptidase (NAALADase)," The Journal of Comparative Neurology 315:217-229 (1992).
Slusher et al., "Selective inhibition of NAALADase, which converts NAAG to glutamate, reduces ischemic brain injury," Nature Medicine, vol. 5, No. 12, Dec. 1999.
Soloviev et al., "PET imaging with 11C-acetate in prostate cancer: a biochemical, radiochemical and clinical perspective," Eur J Nucl Med Mol Imaging (2008) 35:942-949.
Spahn et al., "Wie soll die Hormontherapie beim kastrationsresistenten Prostatakarzinom fortgeführt werden?," Urologe 2012 • 51:15-19.
Sweat et al., "Prostate-Specific Membrane Antigen Expression is Greatest in Prostate Adenocarcinoma and Lymph Node Metastases," Urology 52: 637-640, 1998.
Tang et al., "Prostate targeting ligands based on N-acetylated α-linked acidic dipeptidase," Biochemical and Biophysical Research Communications 307 (2003) 8-14.
Tang et al., "Updated Application of Prostate-Specific Membrane Antigen to the Diagnosis and Treatment of Prostate Cancer," National Journal of Andrology, vol. 14, No. 1, Jan. 2008.
Taylor et al., "Prostate Cancer Targeting Motifs: Expression of anb3, Neurotensin Receptor 1,Prostate Specific Membrane Antigen, and Prostate Stem Cell Antigen in Human Prostate Cancer Cell Lines and Xenografts," The Prostate 72:523-532 (2012).
Testa et al., "Prostate Cancer: Sextant Localization with MR Imaging, MR Spectroscopy, and $^{11}$C-Choline PET/CT," Radiology: vol. 244: No. 3—Sep. 2007.
Thalmann, G., "Fortgeschrittenes Prostatakarzinom," Urologe 2012 • 51:7.
Tykvart et al., "Rational design of urea-based glutamate carboxypeptidase II (GCPII) inhibitors as versatile tools for specific drug targeting and delivery," Bioorganic & Medicinal Chemistry 22 (2014) 4099-4108.
Uprimny et al., "$^{68}$Ga-PSMA ligand PET versus 18F-NaF PET: evaluation of response to 223Ra therapy in a prostate cancer patient," Eur J Nucl Med Mol Imaging (2015) 42:362-363.

(56) References Cited

OTHER PUBLICATIONS

Vallabhajosula et al., "Radioimmunotherapy of Prostate Cancer in Human Xenografts Using Monoclonal Antibodies Specific to Prostate Specific Membrane Antigen (PSMA): Studies in Nude Mice," The Prostate 58:145-155 (2004).
Vavere et al., "1-11C-Acetate as a PET Radiopharmaceutical for Imaging Fatty Acid Synthase Expression in Prostate Cancer," J Nucl Med 2008; 49:327-334.
Wang et al., "Bioisosterism of urea-based GCPII inhibitors: Synthesis and structure—activity relationship studies," Bioorganic & Medicinal Chemistry Letters 20 (2010) 392-397.
Weineisen et al., "Synthesis and preclinical evaluation of DOTAGA-conjugated PSMA ligands for functional imaging and endoradiotherapy of prostate cancer," EJNMMI Research 2014, 4:63.
Weissbach, L. "Welche Inhalte sollte eine "living guideline "besetzen?," Urologe 2012 • 51:57-59.
Whitaker et al., "N-acetyl-L-aspartyl-L-glutamate peptidase-like 2 is overexpressed in cancer and promotes a pro-migratory and pro-metastatic phenotype," Oncogene (2014) 33, 5274-5287.
Wiehr et al., "Pharmacokinetics and PET Imaging Properties of Two Recombinant Anti-PSMA Antibody Fragments in Comparison to their Parental Antibody," The Prostate 74:743-755 (2014).
Wright et al., "Expression of Prostate-Specific Membrane Antigen in Normal, Benign, and Malignant Prostate Tissues," Urol Oncol 1995;1:18-28.
Wu et al., "The molecular pruning of a phosphoramidate peptidomimetic inhibitor of prostate-specific membrane antigen," Bioorganic & Medicinal Chemistry 15 (2007) 7434-7443.
Yamaguchi et al., "Prostate cancer: a comparative study of $^{11}$C-choline PET and MR imaging combined with proton MR spectroscopy," Eur J Nucl Med Mol Imaging (2005) 32:742-748.
Zaheer et al., "New Agents and Techniques for Imaging Prostate Cancer," J Nucl Med 2009; 50:1387-1390.
Zechmann et al., "Radiation dosimetry and first therapy results with a 124I/131 I-labeled small molecule (MIP-1095) targeting PSMA for prostate cancer therapy," Eur J Nucl Med Mol Imaging (2014) 41:1280-1292.
Zhang et al., "A Remote Arene-Binding Site on Prostate Specific Membrane Antigen Revealed by Antibody-Recruiting Small Molecules," J. Am. Chem. Soc. 2010, 132, 12711-12716.
Zhang et al., "Prostate Specific Membrane Antigen (PSMA): A Novel Modulator of p38 for Proliferation, Migration, and Survival in Prostate Cancer Cells," The Prostate 73:835-841 (2013).
Hara et al., "Development of $^{18}$F-Fluoroethylcholine for Cancer Imaging with PET: Synthesis, Biochemistry, and Prostate Cancer Imaging," J Nucl Med 2002; 43:187-199.
Hara et al., "PET Imaging of Prostate Cancer Using Carbon-11-Choline," J Nucl Med 1998;39:990-995.
Examination report No. 1 for Australian Patent Application 2018200419, dated Oct. 24, 2018.
Office action in JP 2017-210775, dated Oct. 26, 2018.
Office action in Eurasian Patent Application 201690495/28, dated Dec. 20, 2018.
De Santis et al., "Role of Chemotherapy in Castration Resistant Prostate Cancer," English translation. Urologe 2012 • 51:39-43.
Heidenreich, A., "Immunotherapy for Metastatic Prostate Cancer—Do We Really Need This?," English translation. Urologe 2012 • 51:32-38.
Kuru et al., "MRI Navigated Stereotactic Prostate Biopsy," English Translation. Urologe 2012 • 51:50-56.
Moltzahn et al., "Bone Metastasis in Prostate Cancer," English translation. Urologe 2012 • 51:20-26.
Omlin et al., "Inhibitors of Androgen and Estrogen Biosynthesis in Castration-Resistant Prostate Cancer," English translation. Urologe 2012 • 51:8-14.
Preusser et al., "Castration-Resistant Prostate Cancer," English translation. Urologe 2012 • 51:27-31.
Reske et al., "Advancement of PET and PET/CT in Prostate Carcinoma," English translation. Urologe 2006 • 45:707-714.
Reske et al., "Nuclear Imaging of Prostate Cancer," English translation. Urologe 2007 • 46:1485-1499.
Reske et al., "PET and PET/CT in Relapsing Prostate Carcinoma," English translation. Urologe 2006 • 45:1240-1250.
Spahn et al., "How Shold Hormone Therapy for Castration-Resistant Prostate Cancer be Continued?," English translation. Urologe 2012 • 51:15-19.
Thalmann, G., "Advanced Prostate Cancer," English translation. Urologe 2012 • 51:7.
Weissbach, L. "Which Components Should 'Living Guidelines' Contain?," English translation. Urologe 2012 • 51:57-59.
Office Action in CA 2924360 dated Jan. 11, 2018.
Office Action in CL 201600883 dated Apr. 12, 2018.
Office Action in CN 201480056250.5 dated Aug. 15, 2018.
Office Action in EA 201690495/28 dated Feb. 10, 2017.
Office Action in GE 2014014132 dated Feb. 2017.
Office Action in GE 2014014132 dated Mar. 2017.
Office Action in KR 10-2016-7012314 dated Mar. 6, 2017.
Office Action in KR 10-2016-7012314 dated Oct. 14, 2017.
Office Action in KR 10-2016-7012314 dated May 2, 2018.
Office Action in CL 201600883 dated Jan. 16, 2019.
Divyya et al., "GCPII modulates oxidative stress and prostate cancer susceptibility through changes in methylation of RASSF1, BNIP3, GSTP1 and Ec-SOD", Mol Biol Rep (2013) 40:5541-5550.
Office Action in GA AP2014014132 dated Jan. 11, 2019.
Office Action in ID P00201603202 dated Jan. 28, 2019.
Office Action in IL 245113 dated Jan. 10, 2019.
Meienhofer et al., "Solid-Phase Synthesis with Attachment of Peptide to Resin through an Amino Acid Side Chain: [8-Lysine]-Vasopressin", Proc Nat. Acad. Sci. USA, vol. 68, No. 5, pp. 1006-1009, May 1971.
Nedrow-Byers et al., "PSMA-argeted SPECT Agents: Mode of Binding Effect on in Vitro Performance", The Prostate 73: 355-362 (2013).
Rong et al., "Molecular Modeling of the Interaction of Glutamate Carboxypeptidase II with Its Potent NAAG-Based Inhibitors", J. Med. Chem. 2002, 45, 4140-4152.
Wu et al., "A mild deprotection procedure for tert-butyl esters and tert-butyl ethers using $ZnBr_2$ in methylene chloride", Tetrahedron Letters 41 (2000) 2847-2849.
European Search Report in EP 18175078.7 dated Sep. 14, 2018.
Dusich et al., "General Approach for the Preparation of Fluorescent PSMA/GCPII Inhibitors", Abstract. Abstract ID: 470, Poster board space: 29. Jul. 2006.
Foss et al., "Synthesis and Validation of a Novel Small-Molecule Fluorescent Probe for PSMA Expression in Human Tumor Ncovasculature" Abstract. Abstract ID: 362. Jul. 2005.

* cited by examiner

CONJUGATES FOR IMAGING

CROSS-REFERENCE TO RELATED APPLICATIONS

This Application is a continuation application of U.S. application Ser. No. 14/989,498 filed Jan. 6, 2016, which claims the benefit of priority under 35 U.S.C. § 119(e) to U.S. Provisional patent application Ser. No. 62/100,677, filed Jan. 7, 2015, the entire disclosures of which are hereby expressly incorporated by reference.

TECHNICAL FIELD

The invention described herein relates to conjugates and compositions for imaging, diagnosing, and/or monitoring diseases using radionuclide-based imaging. In particular, the invention described herein relates to conjugates and compositions for imaging, diagnosing, and/or monitoring diseases using positron emission tomography.

BACKGROUND

Positron emission tomography (PET) is a nuclear imaging methodology that detects pairs of gamma rays emitted indirectly by a positron-producing radionuclide. Because the two emitted gamma rays travel in exactly opposite directions, it is possible to locate their site of origin and thereby reconstruct a three-dimensional image of all positron emitters from a computer analysis of the origins of emitted gamma rays.

Vitamin receptors are overexpressed on certain cells, including many cancer cell types, activated macrophages, and activated monocytes. In particular, folate receptors are overexpressed on many cancers. The folate receptor, a 38 KD GPI-anchored protein that binds the vitamin folic acid with high affinity (<1 nM), is overexpressed on many malignant tissues, including ovarian, breast, bronchial, and brain cancers. It is estimated that 95% of all ovarian carcinomas overexpress the folate receptor. In contrast, with the exception of kidney, choroid plexus, and placenta, normal tissues express low or non-detectable levels of the folate receptor. Most cells also use an unrelated reduced folate carrier to acquire the necessary folic acid.

Following receptor binding of vitamins to vitamin receptors, such as folic acid and analogs and derivatives of folic acid to folate receptors, rapid endocytosis delivers the vitamin into the cell, where it is unloaded in an endosomal compartment at lower pH. Importantly, covalent conjugation of small molecules, proteins, and even liposomes to vitamins and other vitamin receptor binding ligands does not block the ability of the ligand to bind to its receptor, and therefore, such conjugates can readily be delivered to and can enter cells by receptor-mediated endocytosis. Accordingly, imaging agents can be targeted to vitamin receptors, including the folate receptor, for delivery into vitamin receptor expressing cells.

The prostate is a male reproductive organ that functions to produce and store seminal fluid, which provides nutrients and fluids for the survival of sperm introduced into the vagina during reproduction. Like other tissues, the prostate gland may develop either malignant (cancerous) or benign (non-cancerous) tumors. Prostate cancer is reportedly one of the most common male cancers in western societies, and is the second leading form of malignancy among American men.

Prostate-specific membrane antigen (PSMA) is a biomarker that is overexpressed on prostate cancer cells. PSMA is over-expressed in malignant prostate tissues when compared to other organs in the human body such as kidney, proximal small intestine, and salivary glands. PSMA is also expressed on the neovasculature within many non-prostate solid tumors, including lung, colon, breast, renal, liver and pancreatic carcinomas, but not on normal vasculature. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). Though the functions of the intracellular segment and the transmembrane domains are currently reported to be insignificant, the extracellular domain is involved in several distinct activities. For example, PSMA plays a role in the central nervous system, where it metabolizes N-acetyl-aspartyl glutamate (NAAG) into glutamic and N-acetyl aspartic acid. PSMA also plays a role in the proximal small intestine where it removes γ-linked glutamate from poly-γ-glutamated folate and α-linked glutamate from peptides and small molecules.

Though the particular function of PSMA on prostate cancer cells remains unresolved, PSMA is known to undergo rapid internalization into the cell, similar to cell surface bound receptors like vitamin receptors. PSMA is internalized through clathrin-coated pits and subsequently can either recycle to the cell surface or enter lysosomes. Accordingly, imaging agents can be targeted to PSMA for delivery into PSMA expressing cells, such as prostate cancer cells.

SUMMARY

It has been discovered herein that the conjugates and compositions described herein, comprising folate or a PSMA ligand, are useful for targeting and delivering radionuclides for diagnosing, imaging, and/or monitoring various diseases using PET imaging.

Several illustrative embodiments are described by the following clauses:
1. A conjugate of the formula
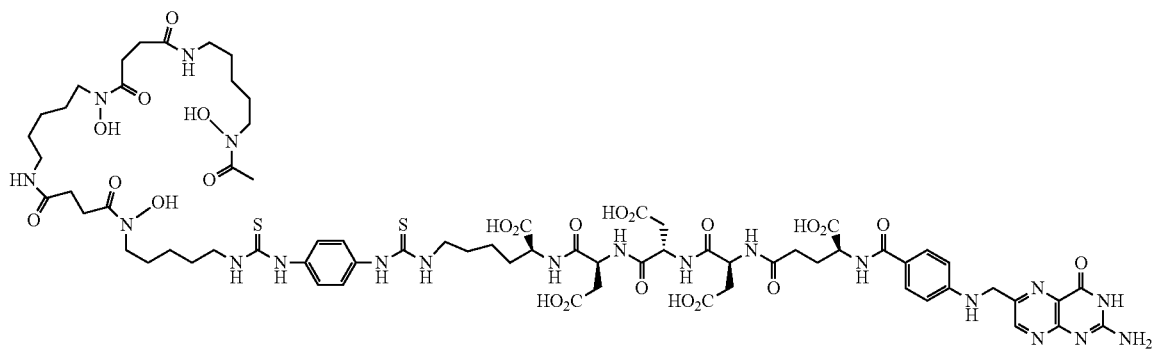 [SMILES: CC(=O)N(O)CCCCCNC(=O)CCC(=O)N(O)CCCCCNC(=O)CCC(=O)N(O)CCCCCNC(=S)Nc1ccc(NC(=S)NCCCC[C@H](NC(=O)[C@H](CC(=O)O)NC(=O)[C@H](CC(=O)O)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cc1]
or a pharmaceutically acceptable salt thereof.
2. A conjugate of the formula
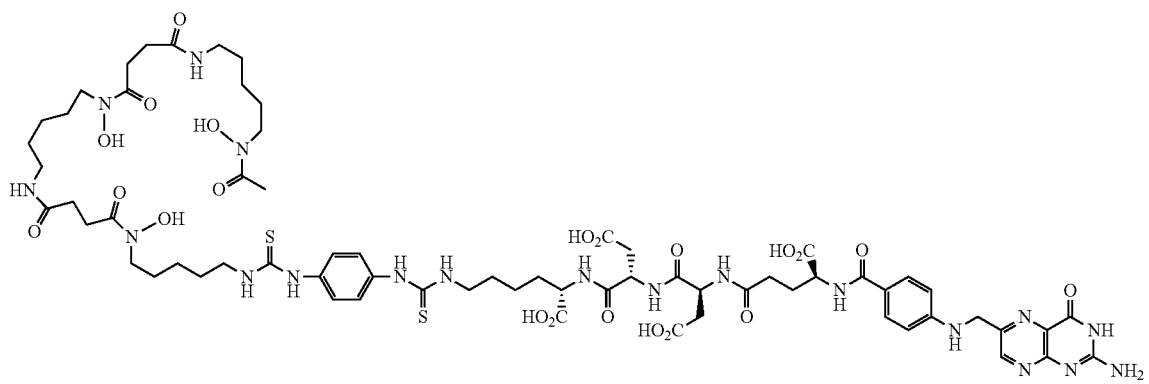 [SMILES: CC(=O)N(O)CCCCCNC(=O)CCC(=O)N(O)CCCCCNC(=O)CCC(=O)N(O)CCCCCNC(=S)Nc1ccc(NC(=S)NCCCC[C@H](NC(=O)[C@H](CC(=O)O)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cc1]
or a pharmaceutically acceptable salt thereof.
3. A conjugate of the formula
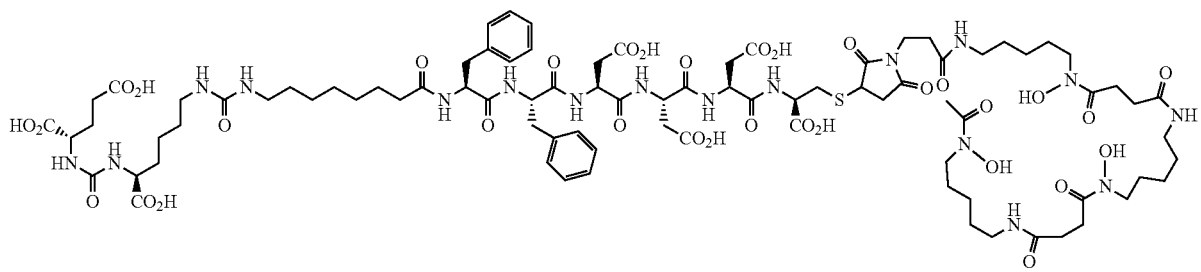 [SMILES: CC(=O)N(O)CCCCCNC(=O)CCC(=O)N(O)CCCCCNC(=O)CCC(=O)N(O)CCCCCNC(=O)CCN1C(=O)CC(SC[C@H](NC(=O)[C@H](CC(=O)O)NC(=O)[C@H](CC(=O)O)NC(=O)[C@H](CC(=O)O)NC(=O)[C@H](Cc2ccccc2)NC(=O)[C@H](Cc2ccccc2)NC(=O)CCCCCCCNC(=O)NCCCC[C@H](NC(=O)N[C@@H](CCC(=O)O)C(=O)O)C(=O)O)C(=O)O)C1=O]
or a pharmaceutically acceptable salt thereof.

4. A conjugate of the formula

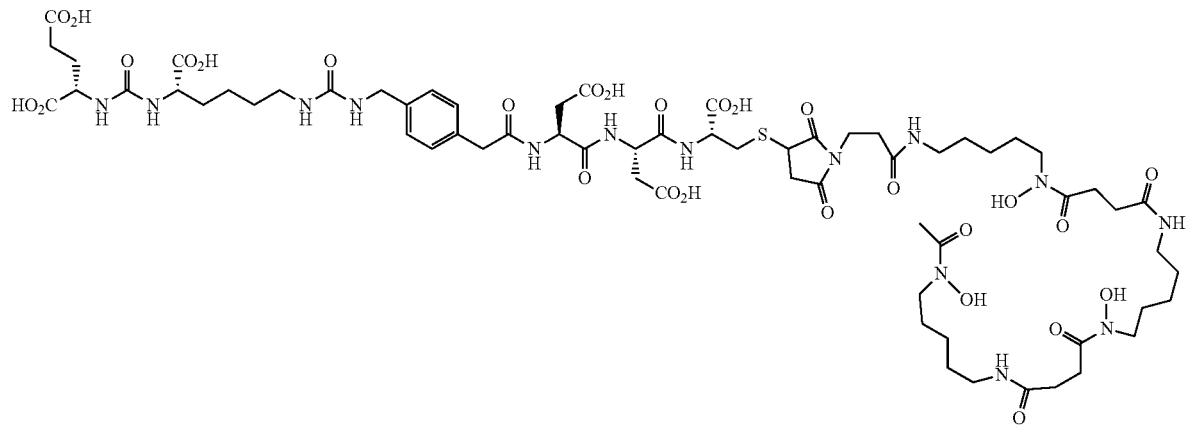 [SMILES: CC(=O)N(O)CCCCCNC(=O)CCC(=O)N(O)CCCCCNC(=O)CCC(=O)N(O)CCCCCNC(=O)CCN1C(=O)CC(SC[C@H](NC(=O)[C@H](CC(=O)O)NC(=O)[C@H](CC(=O)O)NC(=O)Cc2ccc(CNC(=O)NCCCC[C@H](NC(=O)N[C@@H](CCC(=O)O)C(=O)O)C(=O)O)cc2)C(=O)O)C1=O]

or a pharmaceutically acceptable salt thereof.

5. A conjugate of the formula

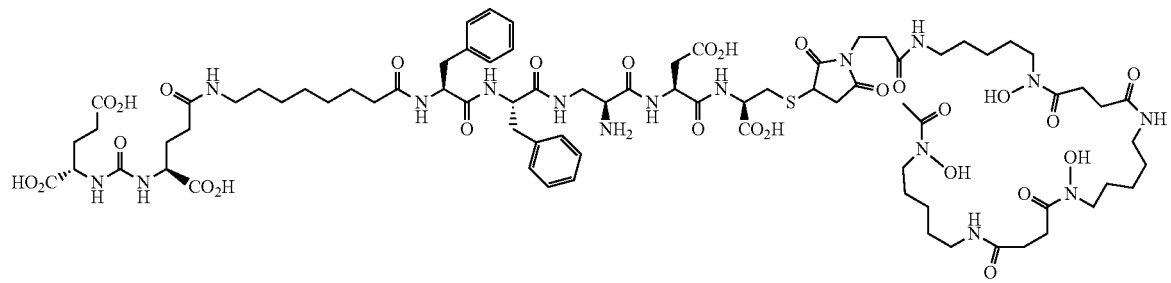

or a pharmaceutically acceptable salt thereof.

6. The conjugate, or pharmaceutically acceptable salt thereof, of any of the preceding clauses wherein the conjugate, or pharmaceutically acceptable salt thereof, is complexed with a radionuclide.

7. The conjugate, or pharmaceutically acceptable salt thereof, of clause 6 wherein the radionuclide is a positron emitting radionuclide.

8. The conjugate, or pharmaceutically acceptable salt thereof, of clause 6 or 7 wherein the radionuclide is a metal ion.

9. The conjugate, or pharmaceutically acceptable salt thereof, of clause 8 wherein the metal ion is selected from the group consisting of $^{89}$Zr, $^{45}$Ti, $^{51}$Mn, $^{64}$Cu, $^{62}$Cu, $^{61}$Cu, $^{60}$Cu, $^{63}$Zn, $^{82}$Rb, $^{86}$Y, $^{68}$Ga, and $^{66}$Ga ions.

10. The conjugate, or pharmaceutically acceptable salt thereof, of any one of clause 8 to 9 wherein the metal ion is a gallium ion.

11. The conjugate, or pharmaceutically acceptable salt thereof, of any one of clauses 8 to 10 wherein the metal ion is a $^{66}$Ga ion.

12. The conjugate, or pharmaceutically acceptable salt thereof, of any one of clauses 8 to 10 wherein the metal ion is a $^{68}$Ga ion.

13. The conjugate, or pharmaceutically acceptable salt thereof, of any one of clauses 8 to 9 wherein the metal ion is a zirconium ion.

14. The conjugate, or pharmaceutically acceptable salt thereof, of clause 13 wherein the metal ion is an $^{89}$Zr ion.

15. The conjugate, or pharmaceutically acceptable salt thereof, of any one of clauses 8 to 9 wherein the metal ion is a copper ion.

16. The conjugate, or pharmaceutically acceptable salt thereof, of clause 15 wherein the metal ion is a $^{64}$Cu ion.

17. A composition comprising the conjugate, or a pharmaceutically acceptable salt thereof, of any one of clauses 1 to 16, and a pharmaceutically acceptable carrier therefor.

18. A kit comprising the conjugate, or a pharmaceutically acceptable salt thereof, of any one of clauses 1 to 17.

DETAILED DESCRIPTION OF ILLUSTRATIVE EMBODIMENTS

In accordance with the disclosure herein, the embodiments of the enumerated clauses provided in the Summary above, or any combination thereof, are contemplated for combination with any of the embodiments described in the Detailed Description section of this patent application.

In one illustrative and non-limiting embodiment described herein, conjugates and compositions described herein are used for diagnosing, imaging, and/or monitoring various diseases. In another embodiment, uses of conjugates and compositions are described herein for manufacturing medicaments for imaging, diagnosing, and/or monitoring various diseases. In another embodiment, uses of the conjugates and compositions described herein for imaging, diagnosing, and/or monitoring various diseases are provided. In another embodiment, kits are described herein for preparing and/or using the conjugates and compositions described herein for imaging, diagnosing, and/or monitoring various diseases.

The conjugates and compositions described herein are used to image, diagnose, and/or monitor various diseases, such as cancer. In one embodiment, the conjugates or compositions described herein can be used for both human clinical medicine and veterinary applications. Thus, a "patient" can be administered the conjugates or compositions described herein, and the patient can be human or, in the case of veterinary applications, can be a laboratory, agricultural, domestic, or wild animal. In one aspect, the patient can be a human, a laboratory animal such as a rodent (e.g., mice, rats, hamsters, etc.), a rabbit, a monkey, a chimpanzee, a domestic animal such as a dog or a cat, an agricultural animal such as a cow, a horse, a pig, a sheep, a goat, and a wild animal in captivity such as a bear, a panda, a lion, a tiger, a leopard, an elephant, a zebra, a giraffe, a gorilla, a dolphin, and a whale.

In various embodiments, the cancers described herein can be cancers that are tumorigenic, including benign tumors and malignant tumors, or the cancer can be non-tumorigenic. In another embodiment, the cancer can arise spontaneously or by such processes as mutations present in the germline of the patient or by somatic mutations, or the cancer can be chemically-, virally-, or radiation-induced. Exemplary cancers include, but are not limited to, a carcinoma, a sarcoma, a lymphoma, a melanoma, a mesothelioma, a nasopharyngeal carcinoma, a leukemia, an adenocarcinoma, and a myeloma.

In some aspects, the cancer can be lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, leukemia, lymphoma, pleural mesothelioma, cancer of the bladder, Burkitt's lymphoma, cancer of the ureter, cancer of the kidney, neoplasms of the central nervous system, brain cancer, pituitary adenoma, or adenocarcinoma of the gastroesophageal junction.

In various embodiments, the conjugates used for imaging, diagnosing and/or monitoring diseases, such as cancer, can be a conjugate of the formula

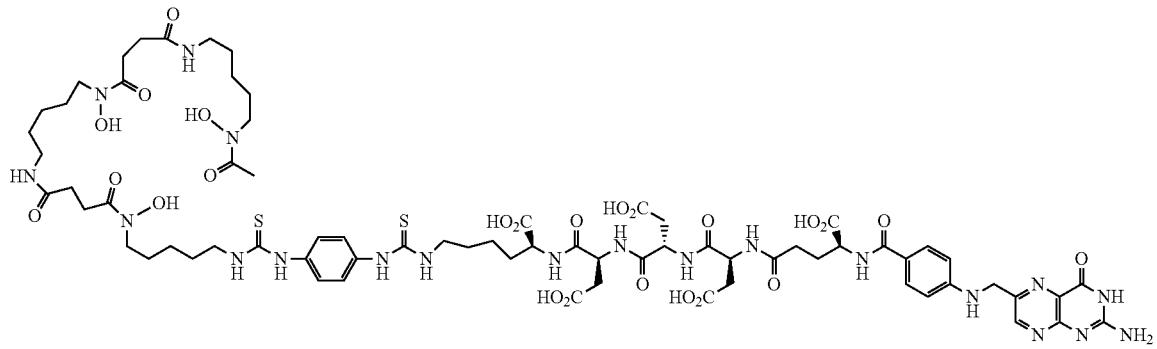 [SMILES: CC(=O)N(O)CCCCCNC(=O)CCC(=O)N(O)CCCCCNC(=O)CCC(=O)N(O)CCCCCNC(=S)Nc1ccc(NC(=S)NCCCC[C@H](NC(=O)[C@H](CC(=O)O)NC(=O)[C@H](CC(=O)O)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cc1]

or a pharmaceutically acceptable salt thereof,

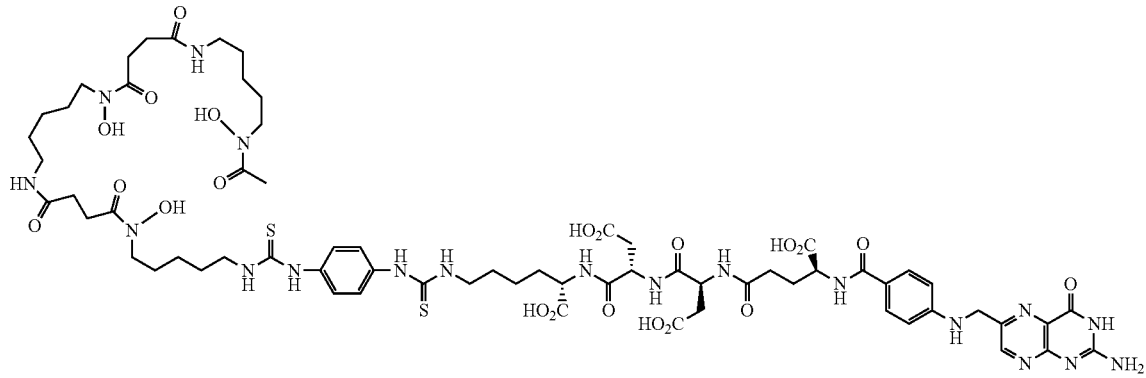 [SMILES: CC(=O)N(O)CCCCCNC(=O)CCC(=O)N(O)CCCCCNC(=O)CCC(=O)N(O)CCCCCNC(=S)Nc1ccc(NC(=S)NCCCC[C@H](NC(=O)[C@H](CC(=O)O)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cc1]

or a pharmaceutically acceptable salt thereof,

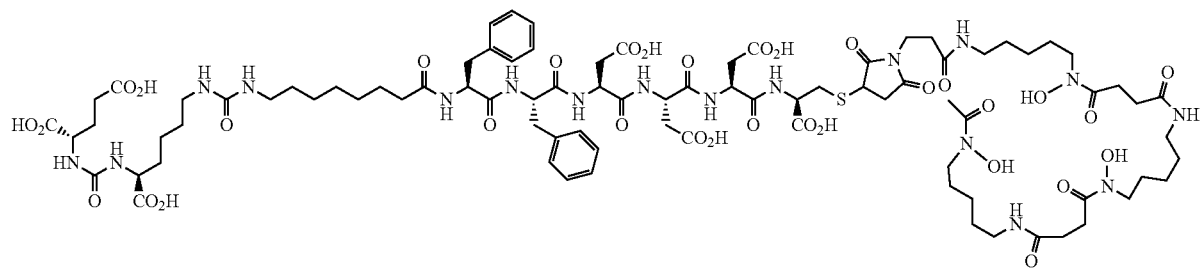 [SMILES: CC(=O)N(O)CCCCCNC(=O)CCC(=O)N(O)CCCCCNC(=O)CCC(=O)N(O)CCCCCNC(=O)CCN1C(=O)CC(SC[C@H](NC(=O)[C@H](CC(=O)O)NC(=O)[C@H](CC(=O)O)NC(=O)[C@H](CC(=O)O)NC(=O)[C@H](Cc2ccccc2)NC(=O)[C@H](Cc2ccccc2)NC(=O)CCCCCCCNC(=O)NCCCC[C@H](NC(=O)N[C@@H](CCC(=O)O)C(=O)O)C(=O)O)C(=O)O)C1=O]

or a pharmaceutically acceptable salt thereof,

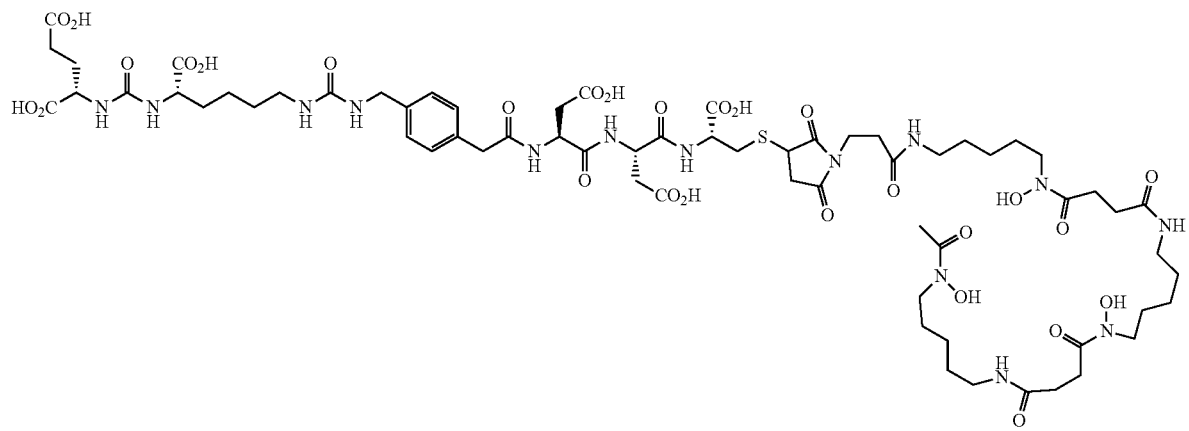 [SMILES: CC(=O)N(O)CCCCCNC(=O)CCC(=O)N(O)CCCCCNC(=O)CCC(=O)N(O)CCCCCNC(=O)CCN1C(=O)CC(SC[C@H](NC(=O)[C@H](CC(=O)O)NC(=O)[C@H](CC(=O)O)NC(=O)Cc2ccc(CNC(=O)NCCCC[C@H](NC(=O)N[C@@H](CCC(=O)O)C(=O)O)C(=O)O)cc2)C(=O)O)C1=O]

or a pharmaceutically acceptable salt thereof, or

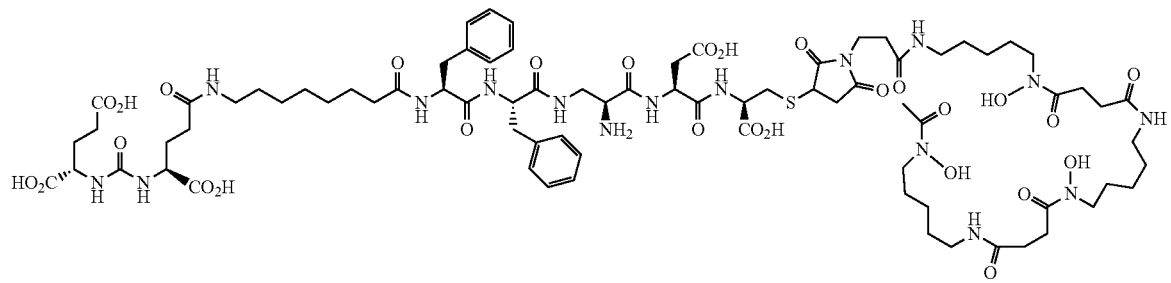

or a pharmaceutically acceptable salt thereof.

In each of the conjugate and composition embodiments described herein, the formulae may include not only all pharmaceutically acceptable salts of the conjugates, but also may include any and all hydrates and/or solvates of the conjugates. In another embodiment, certain functional groups, such as the hydroxy, amino, and like groups form complexes and/or coordination compounds with water and/or various solvents, in the various physical forms of the conjugates described herein. Accordingly, in some embodiments, the above formulae are to be understood to be a description of such hydrates and/or solvates, including pharmaceutically acceptable solvates.

In each of the foregoing and each of the following embodiments, the conjugates described herein may include each possible isomer, such as stereoisomers and geometric isomers, both individually and in any and all possible mixtures, of the formulae described herein. In each of the foregoing and each of the following embodiments, the conjugates may include any and all crystalline forms, partially crystalline forms, and non-crystalline and/or amorphous forms of the conjugates.

As used herein, the term "solvates" refers to conjugates described herein complexed with a solvent molecule. In one embodiment, the conjugates described herein may form such complexes with solvents by simply mixing the conjugates with a solvent, or dissolving the conjugates in a solvent. In the embodiment where the conjugates are to be used as pharmaceuticals, such solvents can be pharmaceutically acceptable solvents. In another embodiment, where the conjugates are to be used as pharmaceuticals, the relative amount of solvent that forms the solvate should be less than established guidelines for such pharmaceutical uses, such as less than International Conference on Harmonization (ICH)

Guidelines. In yet another embodiment, the solvates may be isolated from excess solvent by evaporation, precipitation, and/or crystallization. In some embodiments, the solvates are amorphous, and in other embodiments, the solvates are crystalline.

In the conjugates described herein, the imaging moiety for producing, for example, a PET image may include one or more positron-emitting radionuclides, such as, but not limited to, radionuclides selected from the group consisting of $^{89}Zr$, $^{45}Ti$, $^{51}Mn$, $^{64}Cu$, $^{62}Cu$, $^{61}Cu$, $^{60}Cu$, $^{63}Zn$, $^{82}Rb$, $^{86}Y$, $^{68}Ga$, and $^{66}Ga$. In another embodiment, the radionuclide is a metal ion, such as a positron-emitting metal ion. In another embodiment, the radionuclide is a gallium ion, such as a positron-emitting gallium ion. In another embodiment, the radionuclide is selected from the group consisting of $^{89}Zr$, $^{64}Cu$, $^{68}Ga$, and $^{66}Ga$. In another illustrative embodiment, the radionuclide is selected from the group consisting of $^{89}Zr$, $^{64}Cu$, and $^{68}Ga$. In another embodiment, the radionuclide is $^{68}Ga$ or $^{89}Zr$. In another embodiment in each of the foregoing and following embodiments described herein, the radionuclide is $^{68}Ga$. In another embodiment in each of the foregoing and following embodiments described herein, the radionuclide is $^{89}Zr$. In another embodiment in each of the foregoing and following embodiments described herein, the radionuclide is $^{64}Cu$. In one aspect, factors that may influence selection of a suitable radionuclide include sufficient half-life of the positron-emitting radionuclide to permit preparation of a diagnostic composition in a pharmaceutically acceptable carrier prior to administration to the patient, and sufficient remaining half-life to yield sufficient activity to permit extra-corporeal imaging by a PET scan. In yet another aspect, a suitable radionuclide should have a sufficiently short half-life to limit patient exposure to unnecessary radiation.

Illustrative positron-decaying radionuclides having suitable half-lives include $^{45}Ti$, half-life about 3 hours; $^{61}Cu$, half-life about 3.4 hours; $^{63}Zn$, half-life about 38 minutes; $^{82}Rb$, half-life about 2 minutes; $^{68}Ga$, half-life about 68 minutes, $^{66}Ga$, half-life about 9.5 hours; and $^{89}Zr$, half-life about 78.4 hours.

In other embodiments, pharmaceutically acceptable salts of the conjugates are described. In one aspect, pharmaceutically acceptable salts of the conjugates described herein include acid addition and base salts thereof. Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one embodiment, the conjugates described herein may be administered as a formulation in association with one or more pharmaceutically acceptable carriers. In one illustrative aspect, the carriers can be excipients. In one embodiment, the choice of carrier will to a large extent depend on factors such as the particular mode of administration, the effect of the carrier on solubility and stability, and the nature of the dosage form. In one illustrative aspect, pharmaceutically acceptable carriers for the delivery of the conjugates described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference. In some embodiments, the carrier is suitable for parenteral administration and can be in a sterile aqueous solution.

In one embodiment, a kit is described comprising any of the conjugates, or a pharmaceutically acceptable salt thereof, described herein. In one aspect, such a kit can comprise one or more separate pharmaceutical compositions, at least one of which contains a conjugate, or a pharmaceutically acceptable salt thereof, as described herein. In another embodiment, the kit can comprise a conjugate, or a pharmaceutically acceptable salt thereof, as described herein and one or more separate compositions for labeling the conjugate, or pharmaceutically acceptable salt thereof, with, for example, a metal ion. In another embodiment, means for separately retaining the compositions, such as a container, divided bottle, or divided foil packet are included in the kit. In another embodiment, compositions comprising one or more conjugates described herein, in containers having labels that provide instructions for use of the conjugates are described. In another embodiment, the compositions in the kit are in the form of reconstitutable lyophilizates. In another embodiment, the compositions are in liquid form. In yet another embodiment, the compositions are each in a sterile vial or container.

The following examples further illustrate specific embodiments of the invention; however, the following illustrative examples should not be interpreted in any way to limit the invention.

CONJUGATE EXAMPLES

Procedures for Synthesis of Pet Imaging Agents

SYNTHESIS OF EC2418:

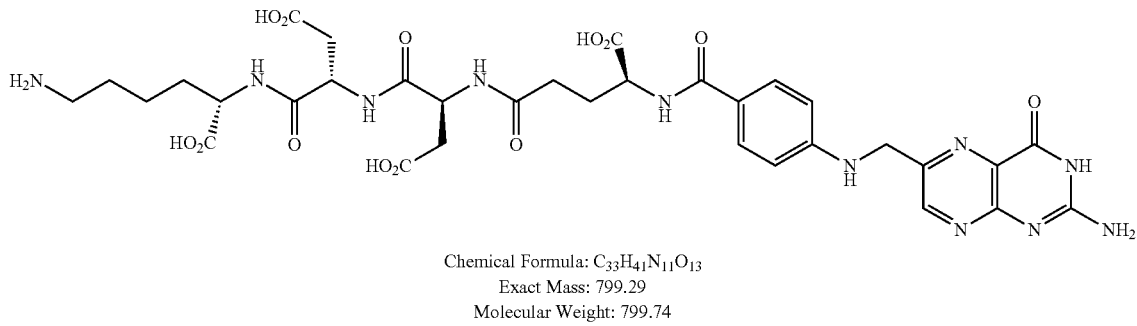

EC2418

Chemical Formula: $C_{33}H_{41}N_{11}O_{13}$
Exact Mass: 799.29
Molecular Weight: 799.74

TABLE

| Reagents for peptide synthesis | | | | |
|---|---|---|---|---|
| Reagents | mmol | equivalent | MW (g/mol) | Amount |
| Fmoc-Lys(MTT)-Resin (0.38 mmol/g) | 1.0 | | | 2.632 g |
| Fmoc-Asp(Ot-Bu)—OH | 2.0 | 2 | 411.5 | 0.822 g |
| Fmoc-Asp(Ot-Bu)—OH | 2.0 | 2 | 411.5 | 0.822 g |
| Fmoc-Glu-Ot-Bu | 2.0 | 2 | 425.5 | 0.850 g |
| $N^{10}$TFA-Pteroic Acid (dissolve in 10 ml DMSO) | 1.5 | 1.5 | 408 | 0.612 g |
| DIPEA | 4.0 | 4 | 129.25 (d = 0.742) | 0.697 mL |
| PyBOP | 2.0 | 2 | 520 | 1.040 g |

Coupling Steps:

Initial Peptide Synthesis On-Resin:

Commercially available 100-200 mesh peptide-loaded resin was utilized in an AAPPTec-sourced peptide synthesizer equipped with DMF, DMF-Peptide, DMF-PyBOP, DMF-DIPEA, and DMF-piperidine solutions. The desired peptide sequence was programmed into the software interface and run in an automated fashion. Upon completion of the sequence, the peptide-loaded resin was removed from the instrument's reaction flask. Analysis of the resin-peptide was conducted by taking a small quantity of beads, cleaving with TFA and analyzing the filtered solution by LCMS (1-50% ACN/10 mM NH4OAc, pH 5).

Cleavage of Peptide from Resin and Purification:

Peptide was cleaved from the loaded resin by a mixture of 95% TFA, 2.5% TIPS, 2.5% $H_2O$. Resin was subjected to cleavage mixture under Argon for 35 min, drained, followed by treatment with fresh cleavage mixture for 5 min and drained (2×). The combined peptide-TFA solution was diluted with ether to precipitate the peptide and collected by centrifuge. Peptide cake was washed with ether and dried. Crude peptide was suspended in water and $Na_2CO_3$ was added and maintained at pH 9-10 for 1 h. The reactions mixture was acidified with 1N HCl to pH 4.0 and purified using a Biotage reverse-phase C18 column (Mobile phase A=0.1% TFA buffer and B=ACN). Product fractions were collected, combined, acetonitrile was removed and the resulting solution freeze-dried to yield EC2418 (496 mg, 62%). LCMS (ESI): $[M+H]^+$=Calculated for $C_{33}H_{41}N_{11}O_{13}$, 800.29; found 800.36

SYNTHESIS OF EC2419:

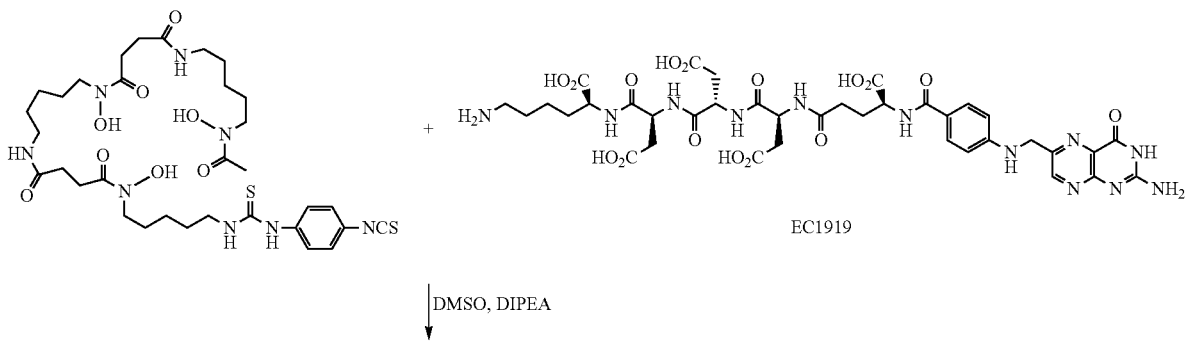

EC1919

DMSO, DIPEA

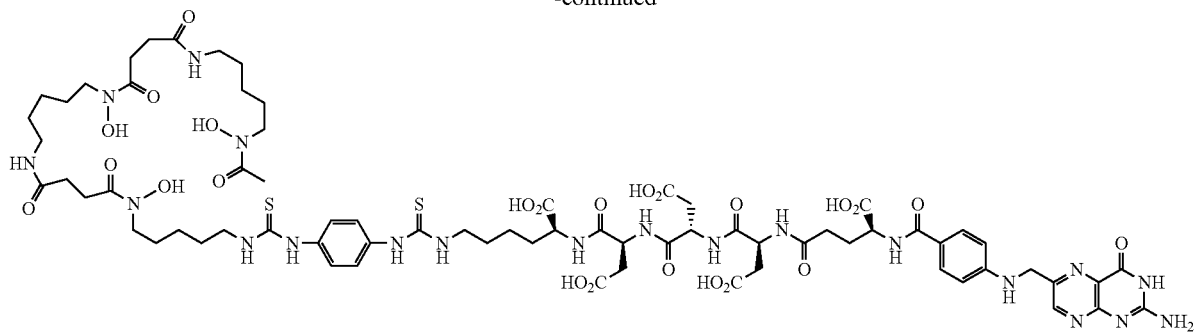

EC2419
Chemical Formula: $C_{70}H_{98}N_{20}O_{24}S_2$
Exact Mass: 1666.65
Molecular Weight: 1667.78

To a solution of EC1919 (213 mg, 0.23 mM) in DMSO (3.0 mL) and DIPEA (0.88 mL) was added P-SCN-Bn-Deferoxamine (175 mg, 0.23 mM) in DMSO (4.0 mL). The solution was stirred at ambient temperature under argon for 3 h. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2419 (308 mg, 80.3%) as a light yellow solid. LCMS (ESI): [M+H]$^+$=Calculated for $C_{70}H_{98}N_{20}O_{24}S_2$, 1667.65; found 1667.79.

To a solution of EC2418 (133.9 mg, 0.167 mM) in DMSO (1.0 mL) and DIPEA (0.58 mL) was added P-SCN-Bn-deferoxamine (105 mg, 0.14 mM) in DMSO (3.0 mL) and stirred at ambient temperature under argon for 3 h. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2420 (165 mg, 75.9%) as a light yellow solid. LCMS (ESI): [M+H]$^+$=Calculated for $C_{66}H_{93}N_{19}O_{21}S_2$, 1552.62; found 1552.71

SYNTHESIS OF EC2420:

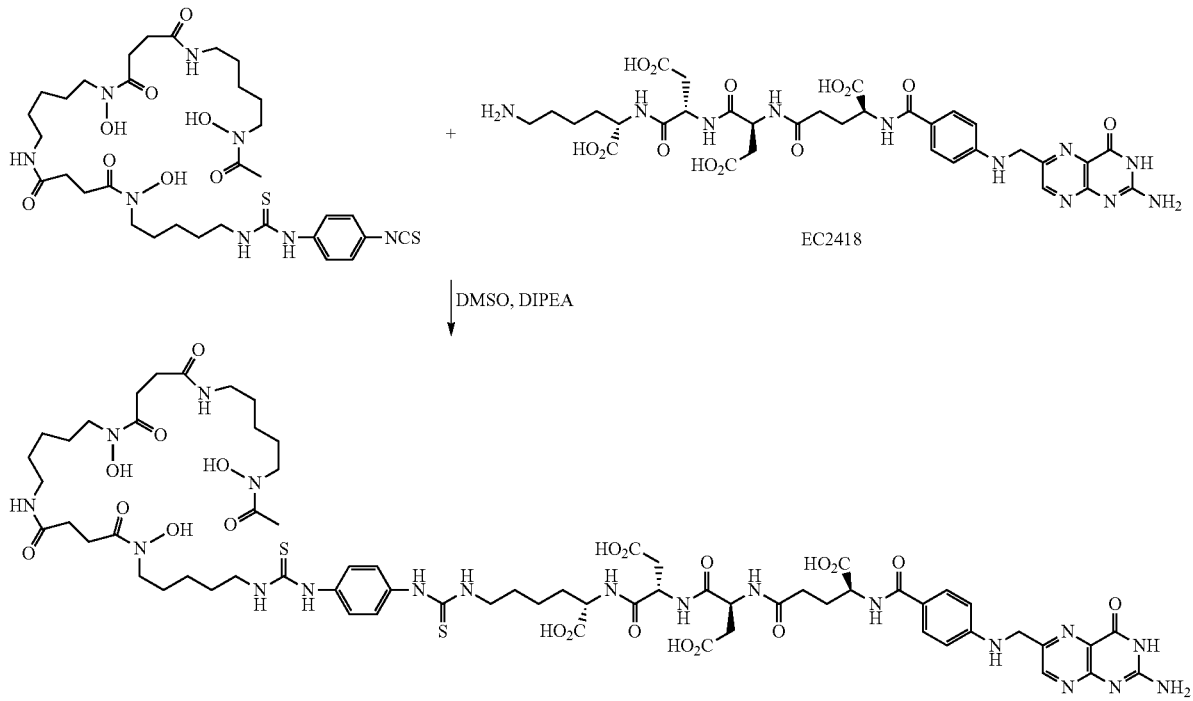

EC2420
Chemical Formula: $C_{66}H_{93}N_{19}O_{21}S_2$
Exact Mass: 1551.62
Molecular Weight: 1552.69

SYNTHESIS OF EC2420:

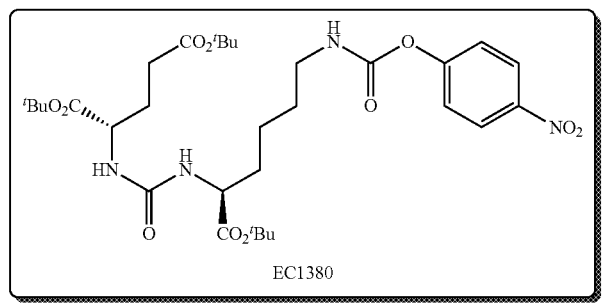

EC1380

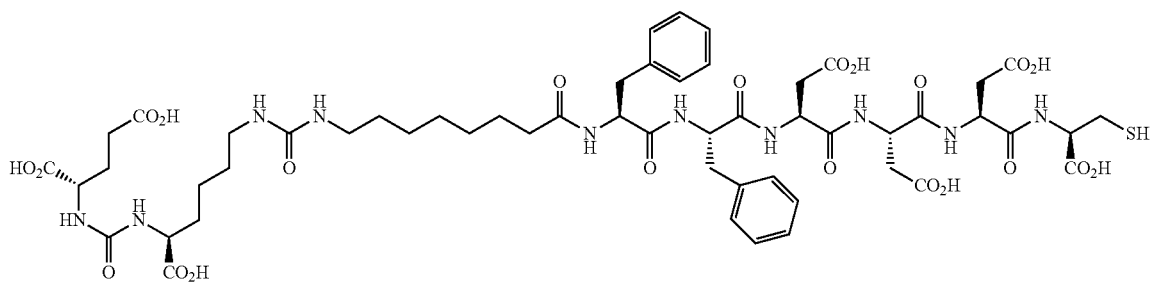

EC2448
Chemical Formula: C54H74N10O22S
Exact Mass: 1246.47
Molecular Weight: 1247.28

TABLE

Reagents for peptide synthesis

| Reagents | mmol | equivalent | MW (g/mol) | Amount |
|---|---|---|---|---|
| Fmoc-Cys(trt)-Resin (0.60 mmol/g) | 0.5 | | | 0.833 g |
| Fmoc-Asp(Ot-Bu)—OH | 1.0 | 2 | 411.5 | 0.411 g |
| Fmoc-Asp(Ot-Bu)—OH | 1.0 | 2 | 411.5 | 0.411 g |
| Fmoc-Asp(Ot-Bu)—OH | 1.0 | 2 | 411.5 | 0.411 g |
| Fmoc-Phe-OH | 1.0 | 2 | 387.4 | 0.387 g |
| Fmoc-Phe-OH | 1.0 | 2 | 387.4 | 0.387 g |
| Fmoc-8-aminocaprylic Acid | 1.0 | 2 | 381.4 | 0.381 g |
| EC1380 | 1.0 | 2 | 652.7 | 0.653 g |
| DIPEA | 2.0 | 4 | 129.25 (d = 0.742) | 0.348 mL |
| PyBOP | 1.0 | 2 | 520 | 0.520 g |

Coupling Steps:
Initial Peptide Synthesis On-Resin:

Commercially-available 100-200 mesh peptide-loaded resin was utilized in an AAPPTec-sourced peptide synthesizer equipped with DMF, DMF-Peptide, DMF-PyB OP, DMF-DIPEA, and DMF-piperidine solutions. The desired peptide sequence, except EC1380, was programmed into the software interface and run in an automated fashion. Upon completion of the sequence, the peptide-loaded resin was removed from the instrument's reaction flask. Analysis of the resin-peptide was conducted by taking a small quantity of beads, cleaving with TFA and analyzing the filtered solution by LCMS (1-50% ACN/10 mM NH$_4$OAc, pH 5).

Addition of EC1380 To Resin-Bound Peptide:

Resin-bound Peptide obtained through automated synthesis was placed in a traditional bench top solid-phase reaction vessel. N-Fmoc protection was removed using 20% piperidine in DMF under argon for 10 minutes (3×). The resin was then rinsed with DMF (3×), and IPA (3×). The removal of Fmoc was confirmed by Kaiser Test. The resin was then rinsed with DMF (3×) and suspended in DMF, with the addition of 2 eq of EC1380, 2 eq of PyBOP, and 4 eq of DIPEA. After 1-2 h of argon bubbling, the solvent was drained and the resin rinsed with DMF (3×), and IPA (3×). Analysis of the resin-peptide was conducted by taking a small quantity of beads, cleaving with TFA and analyzing the filtered solution by LCMS (1-50% ACN/10 mM NH$_4$OAc, pH 5).

Cleavage of Peptide from Resin and Purification:

Peptide was cleaved from the loaded resin by a mixture of 92.5% TFA, 2.5% TIPS, 2.5% H$_2$O, and 2.5% EDT. Resin was subjected to cleavage mixture under Argon for 35 min, drained, followed by treatment with fresh cleavage mixture for 5 min and drained (2×). The resulting peptide-TFA solution was diluted with ether to precipitate the peptide and collected by centrifuge. Peptide cake was washed with ether and dried. Crude peptide was purified using a Biotage reverse-phase C18 column (Mobile phase A=0.1% TFA buffer and B=ACN). Product fractions were collected, combined, acetonitrile was removed and freeze-dried to yield EC2448 (240 mg, 38.5%) LCMS (ESI): [M+H]$^+$=Calculated for C$_{54}$H$_{74}$N$_{10}$O$_{22}$S, 1247.47; found 1247.51

SYNTHESIS OF EC2450:

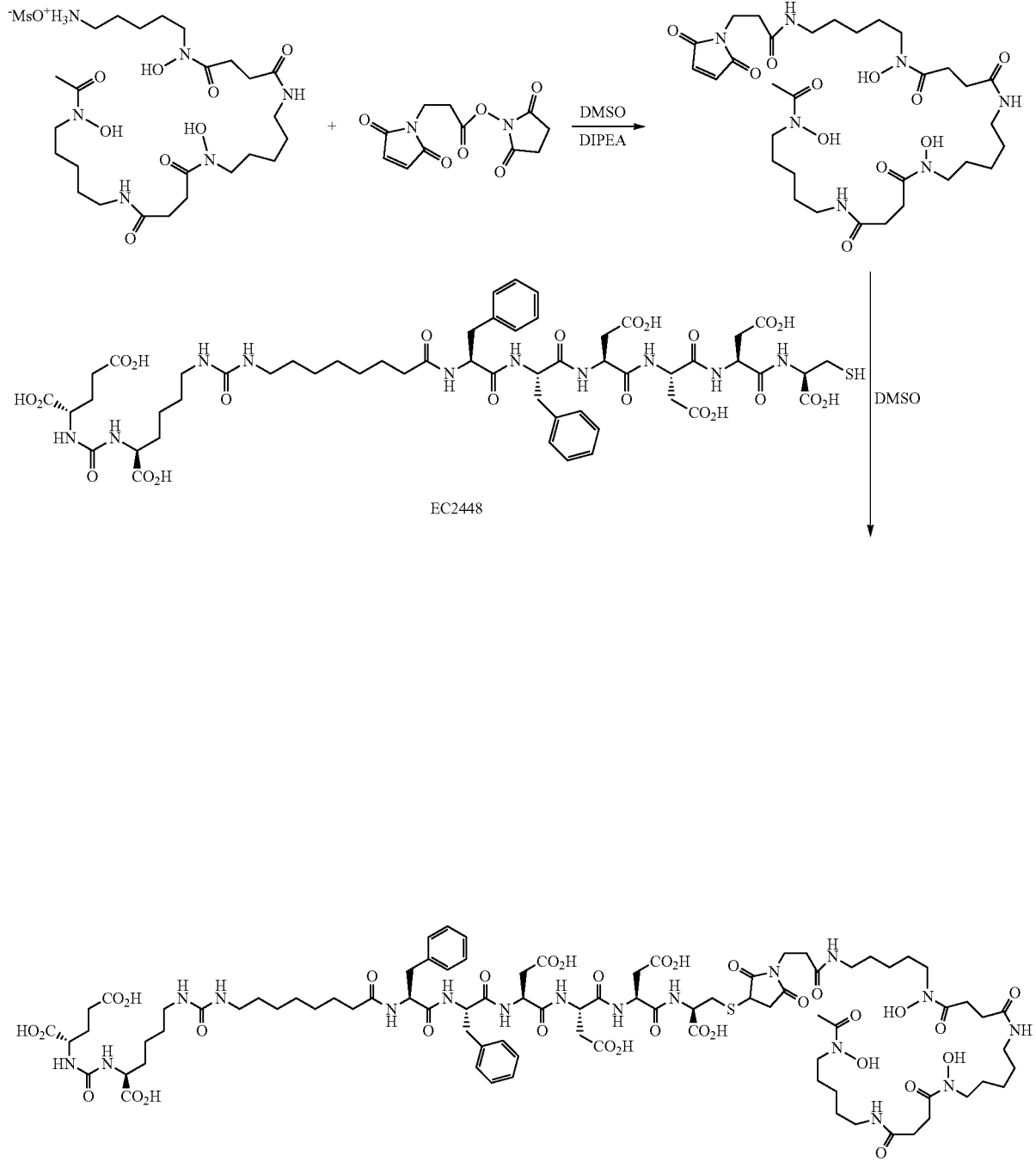

EC2450
Chemical Formula: $C_{86}H_{127}N_{17}O_{33}S$
Exact Mass: 1957.85
Molecular Weight: 1959.09

To a solution of deferoxamine mesylate (65.7 mg, 0.1 mM) in DMSO (0.3 mL) and DIPEA (0.087 mL) was added β-maleimido-propionic acid N-hydroxysuccinimide ester (26.6 mg, 0.1 mM) in DMSO (0.3 mL) and stirred at ambient temperature under argon for 1 h. Solution of EC2448 (118.5 mg, 0.095 mM) in DMSO (0.5 mL) and DIPEA (0.26 mL) were added and stirred for additional 30 min. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and freeze-dried to afford the EC2450 (56 mg, 30.1%, over two steps) as a white solid. LCMS (ESI): $[M-2H]^{2-}$=Calculated for $C_{86}H_{127}N_{17}O_{33}S$, 978.54; found 978.55

SYNTHESIS OF EC2458:

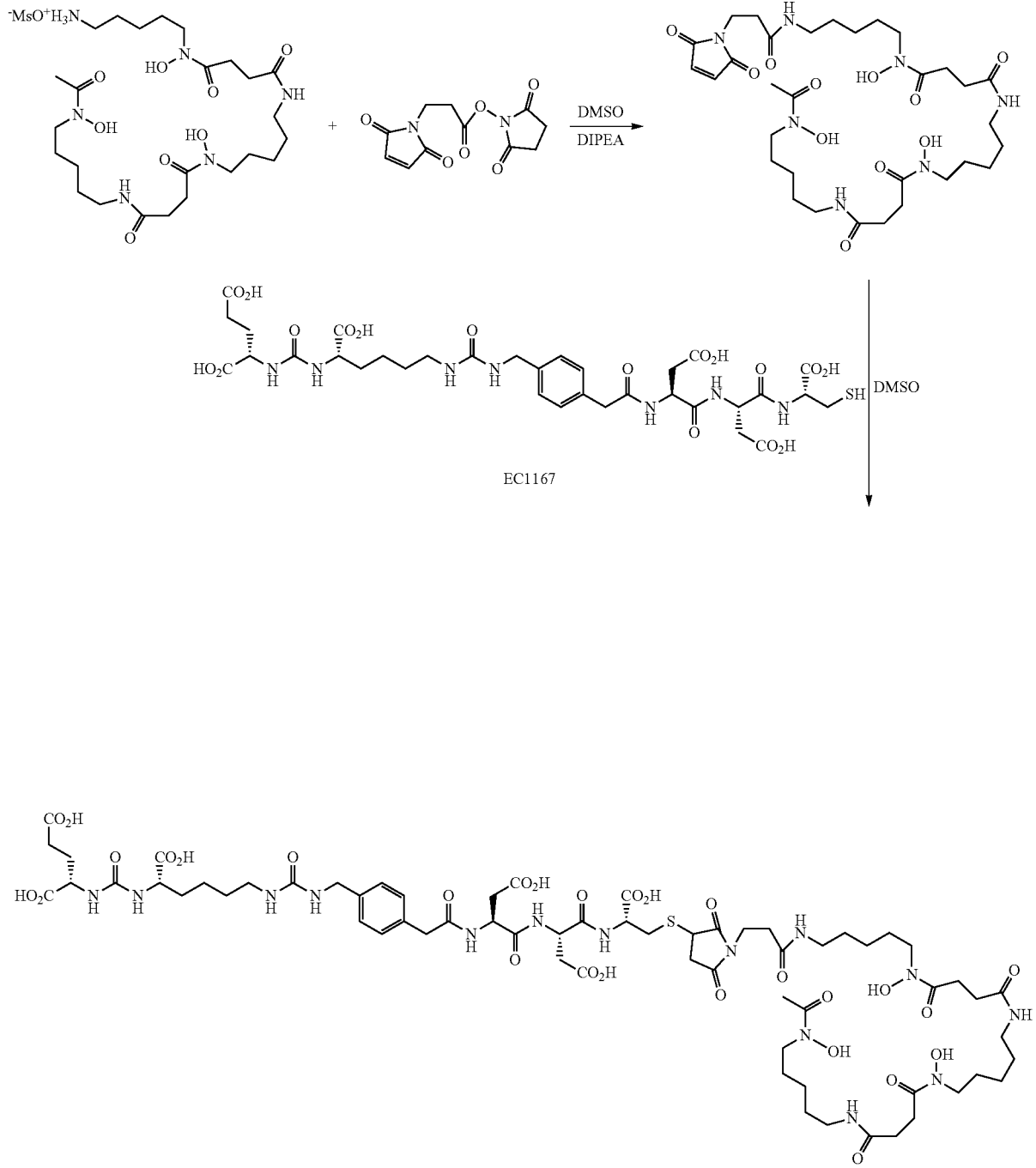

EC2458
Chemical Formula: $C_{65}H_{98}N_{14}O_{28}S$
Exact Mass: 1554.64
Molecular Weight: 1555.62

To a solution of deferoxamine mesylate (65.7 mg, 0.1 mM) in DMSO (0.3 mL) and DIPEA (0.087 mL) was added β-maleimido-propionic acid N-hydroxysuccinimide ester (26.6 mg, 0.1 mM) in DMSO (0.3 mL) and stirred at ambient temperature under argon for 1 h. Solution of EC1167 (92.8 mg, 0.11 mM) in DMSO (1.0 mL) was added and stirred for additional 3 h. Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2458 as a white solid. LCMS (ESI): $[M-2H]^{2-}$=Calculated for $C_{65}H_{98}N_{14}O_{28}S$, 776.81; found 776.67

SYNTHESIS OF EC2460:

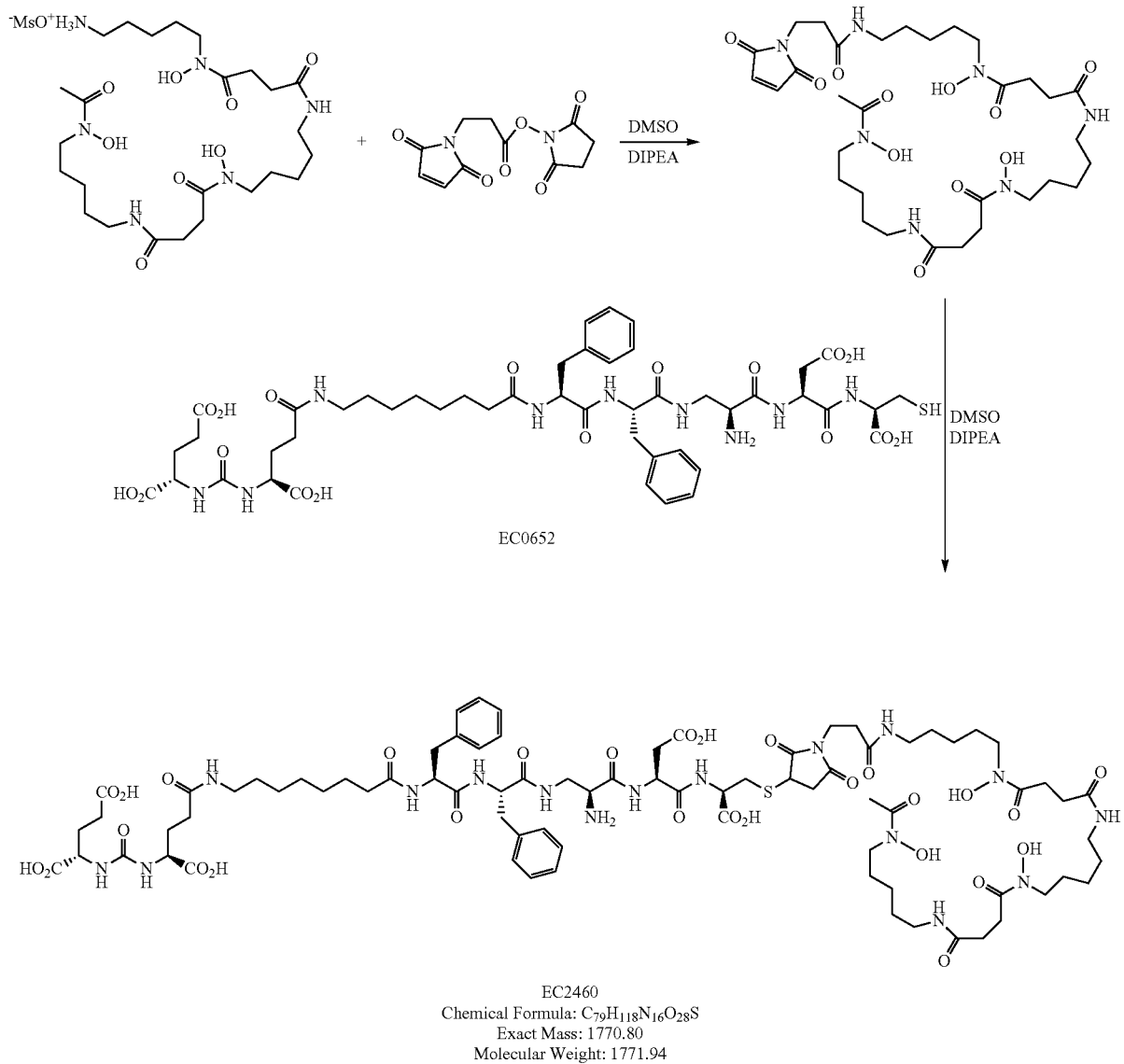

EC2460
Chemical Formula: $C_{79}H_{118}N_{16}O_{28}S$
Exact Mass: 1770.80
Molecular Weight: 1771.94

To a solution of deferoxamine mesylate (65.7 mg, 0.1 mM) in DMSO (0.3 mL) and DIPEA (0.087 mL) was added β-maleimido-propionic acid N-hydroxysuccinimide ester (26.6 mg, 0.1 mM) in DMSO (0.3 mL) and stirred at ambient temperature under argon for 1 h. Solution of EC0652 (116.6 mg, 0.11 mM) in DMSO (0.5 mL) was added and stirred for additional 30 min Reaction mixture was loaded directly onto a Biotage column (mobile phase A=50 mM ammonium bicarbonate buffer, pH=7.0. B=ACN) for purification. Fractions containing the desired product were collected, combined, acetonitrile was removed and the resulting solution freeze-dried to afford the EC2460 (116 mg, 65.4%, over two steps) as a white solid. LCMS (ESI): $[M-2H]^{2-}$ Calculated for $C_{79}H_{118}N_{16}O_{28}S$, 884.97; found 884.86

The deferoxamine conjugates described above may be complexed to a positron emitting metal ion by any of the procedures known to those skilled in the art of producing PET-imaging conjugates and/or compounds.

What is claimed is:

1. A method of imaging a disease in a patient comprising administering a conjugate, or a pharmaceutically acceptable salt thereof, having the formula

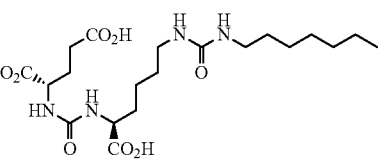

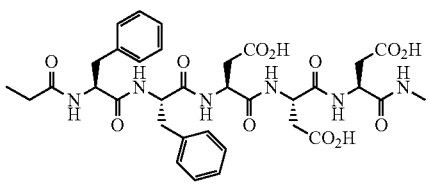

25
-continued
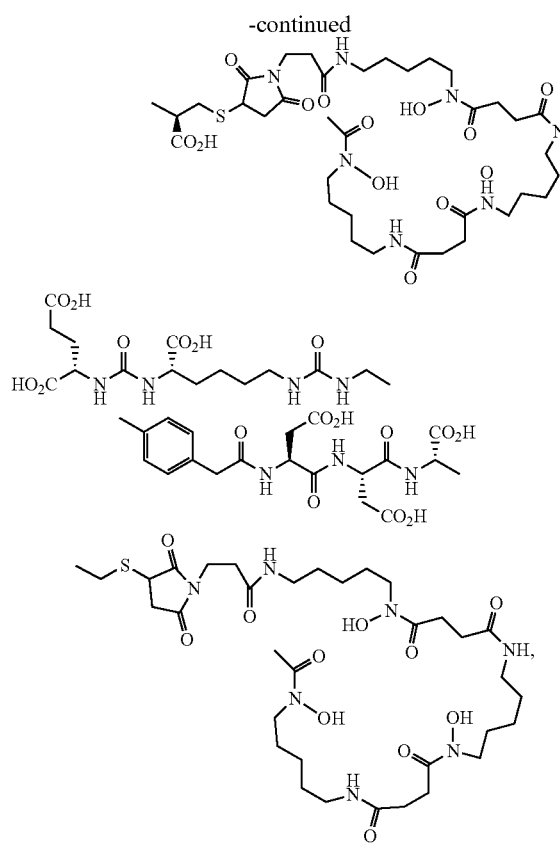
26
-continued
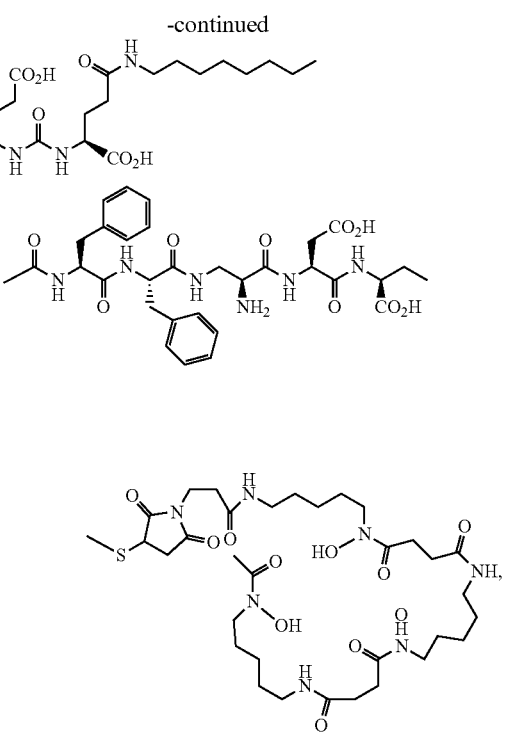
wherein the conjugate is complexed to a radionuclide.
2. The method of claim 1, wherein the conjugate is of the formula
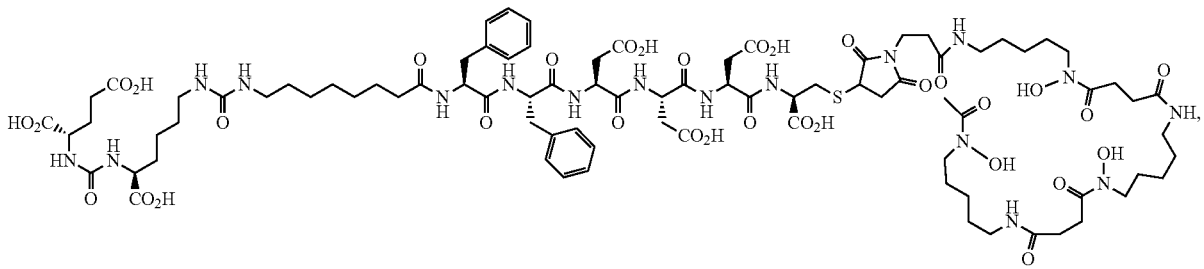 [SMILES: CC(=O)N(O)CCCCCNC(=O)CCC(=O)N(O)CCCCCNC(=O)CCC(=O)N(O)CCCCCNC(=O)CCN1C(=O)CC(SC[C@H](NC(=O)[C@H](CC(=O)O)NC(=O)[C@H](CC(=O)O)NC(=O)[C@H](CC(=O)O)NC(=O)[C@H](Cc2ccccc2)NC(=O)[C@H](Cc2ccccc2)NC(=O)CCCCCCCNC(=O)NCCCC[C@H](NC(=O)N[C@@H](CCC(=O)O)C(=O)O)C(=O)O)C(=O)O)C1=O]
or a pharmaceutically acceptable salt thereof.
3. The method of claim 1, wherein the conjugate is of the formula
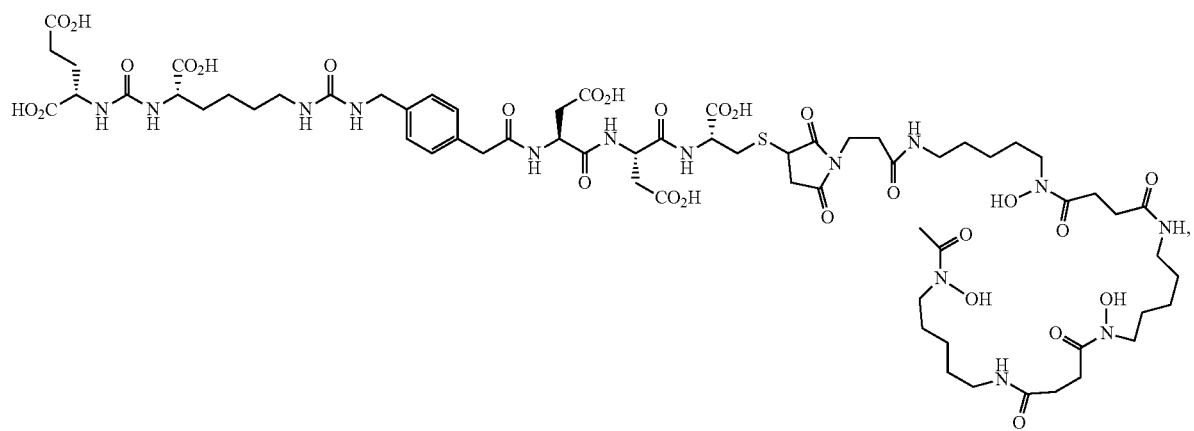 [SMILES: CC(=O)N(O)CCCCCNC(=O)CCC(=O)N(O)CCCCCNC(=O)CCC(=O)N(O)CCCCCNC(=O)CCN1C(=O)CC(SC[C@H](NC(=O)[C@H](CC(=O)O)NC(=O)[C@H](CC(=O)O)NC(=O)Cc2ccc(CNC(=O)NCCCC[C@H](NC(=O)N[C@@H](CCC(=O)O)C(=O)O)C(=O)O)cc2)C(=O)O)C1=O]
or a pharmaceutically acceptable salt thereof.

4. The method of claim 1, wherein the conjugate is of the formula

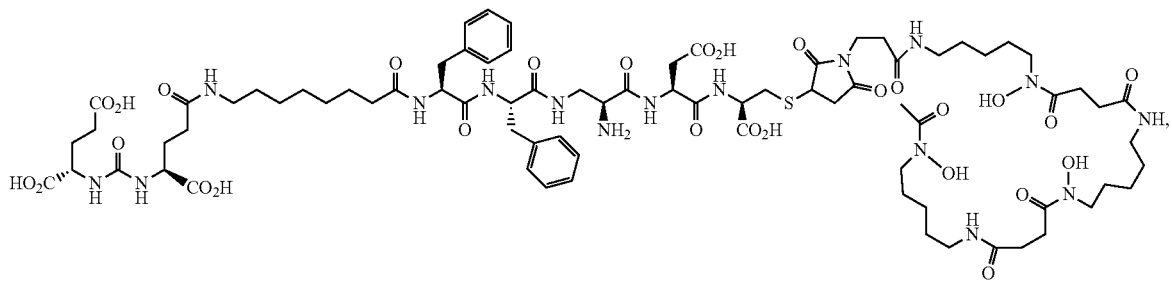

or a pharmaceutically acceptable salt thereof.

5. The method of claim 1, wherein the radionuclide is a positron emitting radionuclide.

6. The method of claim 1, wherein the radionuclide is a metal ion.

7. The method of claim 1, wherein the radionuclide is selected from the group consisting of $^{89}$Zr, $^{45}$Ti, $_{51}$Mn, $^{64}$Cu, $^{62}$Cu, $^{61}$Cu, $^{60}$Cu, $^{63}$Zn, $^{82}$Rb, $^{86}$Y, $^{68}$Ga, and $^{66}$Ga.

8. The method of claim 7, wherein the radionuclide is $^{89}$Zr.

9. The method of claim 1, wherein the imaging is PET imaging.

10. The method of claim 1, wherein the disease is cancer.

11. The method of claim 10, wherein the cancer is tumorigenic.

12. The method of claim 10, wherein the cancer is non-tumorigenic.

13. The method of claim 10, wherein the cancer is selected from the group consisting of lung cancer, bone cancer, pancreatic cancer, skin cancer, cancer of the head, cancer of the neck, cutaneous melanoma, intraocular melanoma uterine cancer, ovarian cancer, endometrial cancer, rectal cancer, stomach cancer, colon cancer, breast cancer, triple negative breast cancer, carcinoma of the fallopian tubes, carcinoma of the endometrium, carcinoma of the cervix, Hodgkin's Disease, cancer of the esophagus, cancer of the small intestine, cancer of the endocrine system, cancer of the thyroid gland, cancer of the parathyroid gland, non-small cell lung cancer, cancer of the adrenal gland, sarcoma of soft tissue, cancer of the urethra, prostate cancer, leukemia, lymphoma, pleural mesothelioma, cancer of the bladder, Burkitt's lymphoma, cancer of the ureter, cancer of the kidney, neoplasms of the central nervous system, brain cancer, pituitary adenoma, and adenocarcinoma of the gastroesophageal junction.

14. The method of claim 10, wherein the cancer is malignant.

15. A method of imaging a disease in a patient comprising administering a composition comprising a conjugate of claim 1, or a pharmaceutically acceptable salt thereof, and a pharmaceutically acceptable carrier.

16. The method of claim 15, wherein the imaging is PET imaging.

17. A method of diagnosing a disease in a patient comprising
a) administering a diagnostic composition comprising a conjugate or a pharmaceutically acceptable salt thereof, having the formula

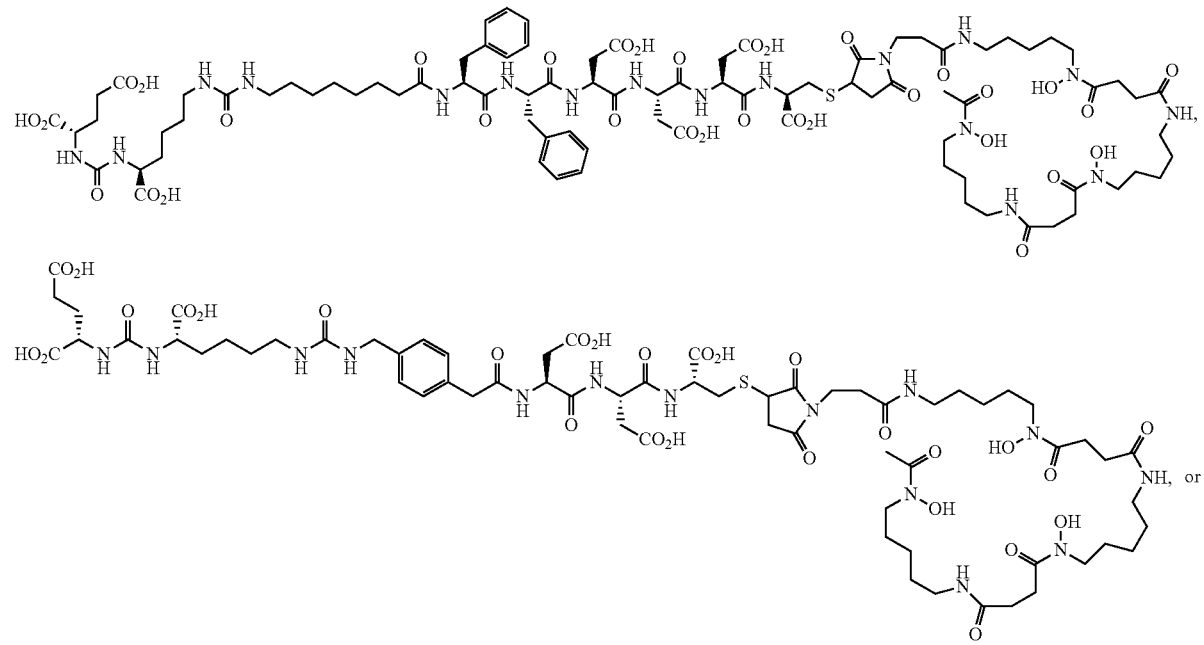

-continued

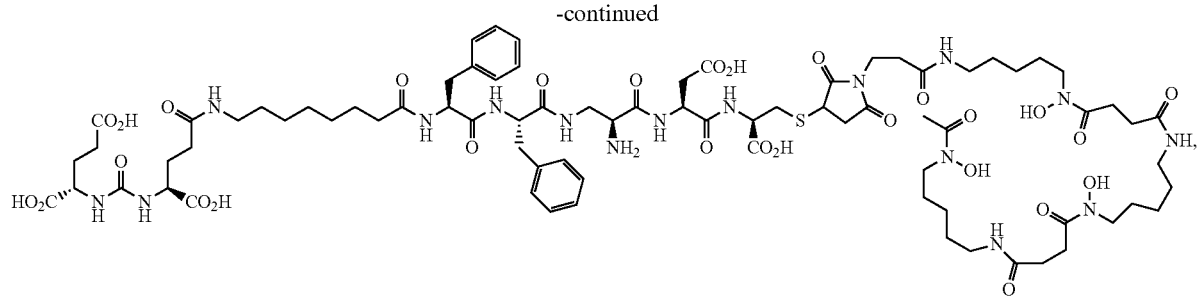

and a pharmaceutically acceptable carrier, wherein the conjugate is complexed to a radionuclide, and b) imaging the patient by a PET scan.

18. The method of claim 17, wherein the radionuclide is selected from the group consisting of $^{89}$Zr, $^{45}$Ti, $^{51}$Mn, $^{64}$Cu, $^{62}$Cu, $^{61}$Cu, $^{60}$Cu, $^{63}$Zn, $^{82}$Rb, $^{86}$Y, $^{68}$Ga, and $^{66}$Ga.

19. The method of claim 18, wherein the radionuclide is $^{68}$Ga, $^{89}$Zr, or $^{64}$Cu.

20. The method of claim 17, wherein the radionuclide of the diagnostic composition has a half-life of about 2 minutes to about 9.5 hours.

21. The method of claim 17, wherein the radionuclide of the diagnostic composition has a half-life of about 78.4 hours.

* * * * *